United States Patent [19]

Romero et al.

[11] Patent Number: 6,084,130

[45] Date of Patent: *Jul. 4, 2000

[54] ARYL SUBSTITUTED BICYCLIC AMINES AS SELECTIVE DOPAMINE D3 LIGANDS

[75] Inventors: Arthur Glenn Romero; William Harold Darlington; Jeffrey A. Leiby, all of Kalamazoo; Chiu-Hong Lin; Susanne R. Haadsma-Svensson, both of Portage; Kerry Anne Cleek, Kalamazoo, all of Mich.

[73] Assignee: Pharmacia & Upjohn Company, Kalamazoo, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 08/859,587

[22] Filed: May 20, 1997

Related U.S. Application Data

[60] Provisional application No. 60/018,794, May 31, 1996.

[51] Int. Cl.[7] .................... C07C 233/00; A61K 31/165
[52] U.S. Cl. .................. 564/163; 564/164; 564/167; 514/619; 514/620
[58] Field of Search ................... 564/163, 164, 564/167; 514/619, 620

[56] References Cited

U.S. PATENT DOCUMENTS

| 4,448,990 | 5/1984 | Bach et al. | 564/167 |
|---|---|---|---|
| 4,788,130 | 11/1988 | Oshiro et al. | 514/661 |
| 4,968,679 | 11/1990 | Junge et al. | 514/222 |
| 5,225,596 | 7/1993 | Carlsson et al. | 564/428 |

FOREIGN PATENT DOCUMENTS

| 27 52 659 A1 | 12/1976 | Denmark . |
| 0 074 903 | 9/1982 | European Pat. Off. . |
| 0 186 087 | 12/1985 | European Pat. Off. . |
| WO 94/21608 | 9/1994 | WIPO . |
| WO 95/04713 | 2/1995 | WIPO . |
| WO 96/23760 | 8/1996 | WIPO . |
| WO96/30333 | 10/1996 | WIPO . |

OTHER PUBLICATIONS

Maillard, Jacques; Delaunay, Pierre, Langlois, Michel et Bernard Portevin (Chimie); Jacques Legeai et Chantal Manuel (Pharmacologie);Synthese de derives amines du tetrahydro–4,5,6,7 benzothiazole, Eur. J. Med. Chem.–Chim. Ther., 1984, 19, No. 5, pp. 451–456.

Murray, PJ; Helden, RM; Johnson, MR; Robertson, GM; Scopes, DIC; Stokes, M; Wadman, S; Whitehead, JWF; Hayes, AG; Kilpatrick, GJ; Large, C; Stubbs, CM; Turpin, MP; Novel 6–Substituted 2–Aminotetralins with Potent and Selective Affinity for the Dopamine $D_3$ Receptor, Bioorganic & Medicinal Chemistry Letters, Vol. 6, No. 4, pp. 403–408, 1996.

Stjernlof, P; Ennis, MD; Hansson, LO; Hoffman, RL; Ghazal, NB; Sundell, S; Smith MW; Svensson,K; Carlsson, A; Wikstrom, H; Structure–Activity Relationships in the 8–Amino–6,7,8,9–tetrahydro–3H–benz[e] indole Ring System. 1. Effects of Substituents in the Aromatic System on Serotonin and Dopamine Receptor Subtypes, J. Med. Chem., 38, 2202–2216 (1995).

Schneider, Claus S., Mierau, Joachin, Dopamine Autoreceptor Agonists: Resolution and Pharmacological Activity of 2,6–Diaminotetrahydrobenzothiazole and an Aminothiazole Analogue of Apomorphine, J. Med. Chem., 1987, 30, 494–498.

*Primary Examiner*—Deborah C. Lambkin
*Attorney, Agent, or Firm*—Bruce Stein; Donald L. Corneglio

[57] ABSTRACT

Compounds and their pharmaceutically acceptable salts suitable for treating central nervous system disorders associated with the dopamine D3 receptor activity of structural Formula I:

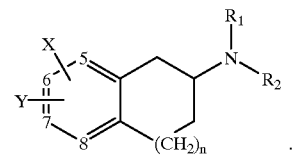

10 Claims, No Drawings

ARYL SUBSTITUTED BICYCLIC AMINES AS SELECTIVE DOPAMINE D3 LIGANDS

CROSS REFERENCE TO RELATED APPLICATIONS

This application claims the benefit of the following provisional application: U.S. Ser. No. 60/018,794, filed May 31, 1996, under 35 USC 119(e)(i).

BACKGROUND OF THE INVENTION

The subject invention is directed toward aryl substituted cyclic amines for the treatment of CNS diseases such as schizophrenia, Parkinson's disease, tardive dyskinesia, obsessive compulsive disorder, depression, and anxiety that preferentially bind to the dopamine D3 receptor. The dopamine D3 receptor was recently cloned by Sokoloff et al. (Nature, 347, 146 (1990)). It was hypothesized that this receptor subtype is of importance for the action of antipsychotics. Interestingly, this receptor shows a relatively high abundance in brain regions associated with emotional and cognitive functions.

Compounds with this profile may be useful in treating CNS disorders, e.g. schizophrenia, mania, depression, geriatric disorders, drug abuse and addiction, Parkinson's disease, anxiety disorders, sleep disorders, circadian rhythm disorders and dementia.

Information Disclosure Statement

PCT Patent Publication No. WO90/07490 describes 2-aminotetralins and 2-aminoindans with aromatic substitution with an $OCH_3$ or OH in conjunction with a Br group.

PCT Patent Publication No. WO95/04713 describes 2-aminoindans which bind to the dopamine D3 receptor.

PCT Patent Application No. PCT/US96/00020 describes 2-aminoindans having sulfonamide substitution on the benzene ring and useful for treating schizophrenia.

U.S. Pat. No. 4,968,679 discloses 2-aminotetralins having a substitution at the 8-position which are serotonin agonist/antagonist.

P J Murry, Novel 6-substituted 2-Aminotetralins, *Bioorg. & Med. Chem. Lett.* 1996, 403 describes compounds having dopamine D3 receptor selectivity that have the benzene ring substituted with 5-methoxy and 6-arylethyl and others with 6-$CH_2SO_2$(4-methoxyphenyl or 4-I-phenyl).

J. Med. Chem. 1987, 30, 494; and Eur. J. Med. Chem. Chim Ther. 1984, 19, 451, disclose cyclic amines similar to the general Formula III if "n" was 2 and "X" was $NH_2$.

SUMMARY OF THE INVENTION

In one aspect the subject invention is directed toward compounds and pharmaceutically acceptable salts of Formula I:

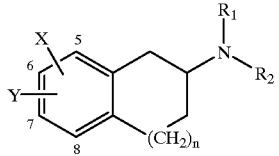

where X and Y are at the 5, 6, or 7 position in place of hydrogen (i.e. replace the hydrogen of a CH) such that:

i) when n is 1 then X can be $(CH_2)_m CONR_4R_5$ (where m is 0 or 1), $(CH_2)_m SO_2NR_4R_5$, $(CH_2)_m NR_4CONHR_5$, $(CH_2)_m NHSO_2R_3$, $(CH_2)_m NHCOR_3$, $C(O)R_4$ or $(CH_2)_m SO_2R_3$ (where for $(CH_2)_m SO_2R_3$, Y is not hydrogen or halogen); and Y is $R_4$, $(CH_2)_p CONR_4R_5$ (where p is 0 or 1), $(CH_2)_p CN$, $(CH_2)_p SO_2NR_4R_5$, $OR_6$, $(CH_2)_p SO_2R_3$, $(CH_2)_p NHSO_2R_3$, halogen, or $(CH_2)_p NHCOR_3$; or ii) when n is 0 or 1 then X and Y can be in ortho-positions relative to each other and are jointly: an N—$R_{10}$ substituted imide such as —C(O)$NR_{10}$C(O)—, —C(O)$NR_4(CH_2)_x NR_{10}$C(O)— (where x is 0 or 1) a lactam such as —$CH_2NR_{10}$C(O)—, —$(CH_2)_2 NR_{10}$C(O)—$CH_2$C(O)$NR_{10}$—, —N($R_3$)—C(O)—N($R_3$)—, —N($R_3$)—C(O)—O—, —N=C($R_7$)—N($R_3$)—, or a cyclic amine such as —$CH_2N(R_8)CH_2$—;

iii) when n is 0 and Y is $OR_9$ then X can be $(CH_2)_m CONR_4R_5$ (where m is 0 or 1), $(CH_2)_m SO_2NR_4R_5$, $(CH_2)_m NR_4CONHR_5$, $(CH_2)_m SO_2R_3$, $(CH_2)_m NHSO_2R_3$, $(CH_2)_m NHCOR_3$ or $C(O)R_4$;

$R_1$ and $R_2$ are independently H, $C_1-C_8$ alkyl including isomeric forms thereof, or $C_1-C_8$ alkylAryl;

$R_3$ is $C_1-C_8$ alkyl, $C_1-C_6$ alkylAryl or Aryl;

$R_4$ and $R_5$ are independently H, $C_1-C_8$ alkyl, $C_1-C_6$ alkylAryl or Aryl;

$R_6$ is H, $SO_2CF_3$, $SO_2C_1-C_8$ alkyl, $SO_2$-$C_1-C_6$alkylAryl, $SO_2$Aryl, $C_1-C_8$alkyl, $C_1-C_6$alkylAryl or Aryl $R_7$ is hydrogen, $CON(R_4)_2$, $SO_2N(R_4)_2$ or $SO_2R_4$;

$R_8$ is $C_1-C_8$ alkyl, $C_1-C_6$ alkylAryl, Aryl, $CON(R_4)_2$, $COR_4$, $SO_2N(R_4)_2$ or $SO_2R_4$ (provided for $CON(R_4)_2$, $COR_4$, $SO_2N(R_4)_2$ or $SO_2R_4$, $R_4$ is not hydrogen);

$R_9$ is $C_2-C_8$ alkyl (optionally substituted with 1 to 3 halogens), $C_1-C_6$ alkylAryl, Aryl; and $R_{10}$ is H, $C_1-C_8$ alkyl, $C_1-C_6$ alkylAryl, Aryl or $(CH_2)_{0-6}SO_2$Aryl.

In another aspect the subject invention is directed toward compounds and pharmaceutically acceptable salts of Formula II:

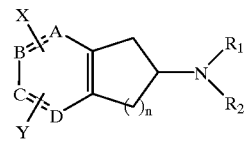

wherein one of A, B, C or D is nitrogen and the remaining positions are CH and n is 1 or 2;

$R_1$ and $R_2$ are independently H, $C_1-C_8$ alkyl and isomeric forms thereof, $C_1-C_8$ alkylAryl;

X and Y can be substituted at positions A, B, C, or D in place of hydrogen (i.e. replace the hydrogen of a CH) wherein i) X is $(CH_2)_m CONR_4R_5$, $(CH_2)_m CN$, $(CH_2)_m SO_2NR_4R_5$, $(CH_2)_m NR_4CONHR_5$, $(CH_2)_m SO_2R_3$, $(CH_2)_m NHSO_2R_3$, $(CH_2)_m NHCOR_3$ or $C(O)R_4$ (where m is 0 or 1, except that where m is 0, Y is not hydrogen or halogen); and Y is $R_4$, $(CH_2)_p CONR_4R_5$, $(CH_2)_p CN$, $(CH_2)_p SO_2NR_4R_5$, $OR_6$, $OSO_2R_3$, $(CH_2)_p SO_2R_3$, $(CH_2)_p NHSO_2R_3$, halogen or $(CH_2)_p NHCOR_3$ (where p is 0 or 1); or ii) X and Y when in ortho-positions relative to each other jointly are an N—$R_4$ substituted imide such as —C(O)$NR_4$C(O)—, a lactam such as —$CH_2NR_4$C(O)— or —$CH_2$C(O)$NR_4$— or a cyclic amine such as —$CH_2NR_4CH_2$—;

$R_3$ is $C_1-C_8$ alkyl, $C_1-C_6$ alkylAryl or Aryl;

$R_4$ and $R_5$ are independently H, $C_1-C_8$ alkyl, $C_1-C_6$ alkylAryl or Aryl; and $R_6$ is H, $SO_2CF_3$, $SO_2CH_3$, $SO_2Aryl$, $C_1$–$C_8$alkyl, $C_1$–$C_6$alkylAryl or Aryl.

In another aspect the subject invention is directed toward compounds and pharmaceutically acceptable salts of Formula III:

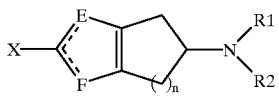

wherein one of E or F is N and the other is S and n is 1 or 2;

$R_1$ and $R_2$ are independently H, $C_1$–$C_8$ alkyl and isomeric forms thereof or $C_1$–$C_8$ alkylAryl;

where X is $(CH_2)_m CONR_4R_5$, $(CH_2)_m CN$, $(CH_2)_m SO_2NR_4R_5$, $CH_2NR_4CONHR_5$, $(CH_2)_m SO_2R_3$, $(CH_2)_m NHSO_2R_3$ or $CH_2NHCOR_3$, $C(O)R_4$;

$R_3$ is $C_1$–$C_8$ alkyl, $C_1$–$C_6$ alkylAryl or Aryl;

$R_4$ and $R_5$ are independently H, $C_1$–$C_8$ alkyl, $C_1$–$C_6$ alkylAryl or Aryl; and where m is 0 or 1.

In another aspect the subject invention is directed toward compounds and pharmaceutically acceptable salts of Formula I, II or III, above, including racemic mixtures and as both enantiomers.

In yet another aspect the subject invention is a method for treating schizophrenia by administering a therapeutically effective amount of a compound of Formula I, II or III to a patient suffering from schizophrenia. The compounds of Formula I, II or III can be administered to a patient suffering from schizophrenia, mania, depression, geriatric disorders, drug abuse and addiction, Parkinson's disease, sleep disorders, circadian rhythm disorders, anxiety disorders or dementia. The compounds can be administered in an amount of from about 0.25 mg to about 100 mg/person.

In yet another aspect, the subject invention is directed toward a method for treating central nervous system disorders associated with the dopamine D3 receptor activity in a patient in need of such treatment comprising administering to the subject a therapeutically effective amount of a Formula I, II or III compound for alleviation of such disorder. Typically, the compound of Formula I, II or III is administered in the form of a pharmaceutical composition comprising a pharmaceutically-acceptable carrier or diluent.

In yet another aspect, the subject invention is directed toward a pharmaceutical composition for treating central nervous system disorders associated with the dopamine D3 receptor activity comprising an effective amount of a compound of Formula I, II or III with a pharmaceutically-acceptable carrier or diluent.

DETAILED DESCRIPTION OF THE INVENTION

The subject invention is directed toward compounds or pharmaceutically acceptable salts of Formula I, II or III as depicted above in either racemic or pure enantiomer forms.

"Alkyl" are one to eight or six carbon atoms such as methyl, ethyl, propyl, butyl, pentyl, hexyl, heptyl, octyl and isomeric forms thereof "Halogen" is an atom of fluorine, chlorine, bromine or iodine.

"Aryl" includes phenyl, pyridinyl, imidazolyl, thiophenyl, oxazolyl, oxadiazole, benzotriazole, benzooxadiazole, thiazole, and isoxazolyl. Aryl can be substituted with one or more fluorine, chlorine, bromine, amino, CN, carboxamido, acetamido, methyl, nitro, sulfonyl, sulfonamido, trifluoromethyl, thifluoromethoxy, O-alkoxy, triflate, or acetyl.

Pharmaceutically acceptable salts include salts of both inorganic and organic acids. The preferred pharmaceutically acceptable salts include salts of the following acids: methanesulfonic, hydrochloric, hydrobromic, sulfuric, phosphoric, nitric, benzoic, citric, tartaric, fumaric or maleic.

The compounds of Formula I, II or III are active orally or parenterally. Orally the Formula I, II or III compounds can be given in solid dosage forms such as tablets or capsules, or can be given in liquid dosage forms such as elixirs, syrups or suspensions as is known to those skilled in the art. It is preferred that the Formula I, II or III compounds be given in solid dosage form and that it be a tablet.

Typically, the compounds of Formula I, II or III can be given in the amount of about 0.5 mg to about 250 mg/person, one to three times a day. Preferably, about 5 to about 50 mg/day in divided doses.

The exact dosage and frequency of administration depends on the particular compound of Formula I, II or III used, the particular condition being treated, the severity of the condition being treated, the age, weight, general physical condition of the particular patient, other medication the individual may be taking as is well known to those skilled in the art and can be more accurately determined by measuring the blood level or concentration of the active compound in the patient's blood and/or the patient's response to the particular condition being treated.

Thus, the subject compounds, along with a pharmaceutically-acceptable carrier, diluent or buffer, can be administrated in a therapeutic or pharmacological amount effective to alleviate the central nervous system disorder with respect to the physiological condition diagnosed. The compounds can be administered intravenously, intramuscularly, topically, transdermally such as by skin patches, buccally or orally to man or other vertebrates.

The compositions of the present invention can be presented for administration to humans and other vertebrates in unit dosage forms, such as tablets, capsules, pills, powders, granules, sterile parenteral solutions or suspensions, oral solutions or suspensions, oil in water and water in oil emulsions containing suitable quantities of the compound, suppositories and in fluid suspensions or solutions.

For oral administration, either solid or fluid unit dosage forms can be prepared. For preparing solid compositions such as tablets, the compound can be mixed with conventional ingredients such as talc, magnesium stearate, dicalcium phosphate, magnesium aluminum silicate, calcium sulfate, starch, lactose, acacia, methylcellulose, and functionally similar pharmaceutical diluent or carrier materials. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. Suspensions can be prepared with an aqueous vehicle with the aid of a suspending agent such as acacia, tragacanth, methylcellulose and the like.

For parenteral administration, fluid unit dosage forms can be prepared utilizing the compound and a sterile vehicle. In preparing solutions, the compound can be dissolved in water for injection and filter sterilized before filling into a suitable vial or ampoule and sealing. Adjuvants such as a local anesthetic, preservative and buffering agents can be dissolved in the vehicle. The composition can be frozen after filling into a vial and the water removed under vacuum. The lyophilized powder can then be sealed in the vial and reconstituted prior to use.

Binding Data for Examples

Competition binding experiments employed eleven dilutions of test compounds of Formula I competing with [$^3$H]-5-(dipropylamino)-5,6-dihydro-4H-imidazo(4,5,1-ij)quinolin-2(1H)-one (R-enantiomer) ("86170") (62 Ci/mmol, 2 nM) and [$^3$H]-spiperone ("SPI") (107 Ci/mmol, 0.5 nM) for D2 and D3 binding sites, respectively. (Lahti, R. A., Eur. J. Pharmacol., 202, 289 (1991)) In each experiment, cloned rat receptors expressed in CHO-K1 cells were used. (Chio, C. L., Nature, 343, 266 (1990); and Huff, R. M., Mol. Pharmacol. 45, 51–60 (1993)). The results are shown in Table I.

TABLE I

| Example # | Receptor | Ligand | Ki (nM) |
| --- | --- | --- | --- |
| 2 | D2-DOP-CLONE | 86170 | 1436 |
|   | D3-DOP-CLONE | SPI | 32 |
| 3 | D2-DOP-CLONE | 86170 | 206 |
|   | D3-DOP-CLONE | SPI | 12 |
| 4 | D2-DOP-CLONE | 86170 | 772 |
|   | D3-DOP-CLONE | SPI | 109 |
| 5 | D2-DOP-CLONE | 86170 | 786 |
|   | D3-DOP-CLONE | SPI | * |
| 6 | D2-DOP-CLONE | 86170 | 1684 |
|   | D3-DOP-CLONE | SPI | 1453 |
| 8 | D2-DOP-CLONE | 86170 | 177 |
|   | D3-DOP-CLONE | SPI | 87 |
| 9 | D2-DOP-CLONE | 86170 | * |
|   | D3-DOP-CLONE | SPI | * |
| 10 | D2-DOP-CLONE | 86170 | 324 |
|   | D3-DOP-CLONE | SPI | 18 |
| 11 | D2-DOP-CLONE | 86170 | >2235 |
|   | D3-DOP-CLONE | SPI | 195 |

*indicates compound was inactive.

Legend of Examples. Formula I wherein n is 1, $R_1$ and $R_2$ are n-propyl, Y is H and X is substituted at the 7 position as follows:

| Ex. # | X | Ex # | X |
| --- | --- | --- | --- |
| 2 | CH$_2$NHSO$_2$-4-CN-phenyl | 3 | CH$_2$NHSO$_2$-4-Cl-phenyl |
| 4 | CH$_2$NHSO$_2$-4-NO$_2$-phenyl | 5 | CH$_2$NHSO$_2$-3-CN-phenyl |
| 6 | CH$_2$NHSO$_2$-4-methyl-imidazole | 8 | CH$_2$NHC(O)-4-Cl-phenyl |
| 9 | CH$_2$NHC(O)-4-CN-phenyl | 10 | NHSO$_2$-4-Cl-phenyl |
| 11 | NHSO$_2$-4-CN-phenyl |   |   |

As was done for Table I, competition binding experiments employed eleven dilutions of test compounds of Formula II competing with [$^3$H]-5-(dipropylamino)-5,6-dihydro-4H-imidazo(4,5,1-ij)quinolin-2(1H)-one (R-enantiomer) ("86170") (62 Ci/mmol, 2 nM) and [$^3$H]-7-OH-DPAT ("7-OH-DPAT") (107 Ci/mmol, 0.5 nM) for D2 and D3 binding sites, respectively. (Lahti, R. A., Eur. J. Pharmacol., 202, 289 (1991)) In each experiment, cloned rat receptors expressed in CHO-K1 cells were used. (Chio, C. L., Nature, 343, 266 (1990); and Huff, R. M., Mol. Pharmacol., 45, 51–60 (1993). Ki values were calculated with the Chen-Prushoff equation. The results are shown in Table II for compounds prepared under Scheme 5.

TABLE II

| COMPOUND # | Receptor | Ligand | Ki (nM) |
| --- | --- | --- | --- |
| 52 | D2-DOP-CLONE | 86170 | 357 |
|   | D3-DOP-CLONE | 7-OH-DPAT | 6 |
| 53 | D2-DOP-CLONE | 86170 | 184 |
|   | D3-DOP-CLONE | 7-OH-DPAT | 3 |

Chemical Synthesis

Scheme 1 and Scheme 2: (Formula I Analogs)

The N-carbomethoxy anhydride prepared from D-aspartic acid (1, Scheme 1) underwent an aluminum chloride mediated Friedel-Crafts reaction with bromobenzene to afford ketone 2. This ketone underwent reduction of the ketone group with triethylsilane catalyzed by titanium tetrachloride, to give 3. This carboxylic acid was converted to the acid chloride which then underwent an aluminum chloride catalyzed Friedel-Crafts cyclization to obtain tetralone 4. This ketone was reduced with triethylsilane, catalyzed by titanium tetrachloride, to give tetralin 5. The carbamate group was saponified with hydroxide to give 7-bromo-2-aminotetralin 6, which was then alkylated to give 7. Treatment of this aryl bromide with t-butyllithium followed by trimethylsilylisocyanate (Tetrahed. Lett. 1975, 981), followed by aqueous hydrolysis, gave carboxamide 8. Refluxing this carboxamide in THF with borane resulted in reduction to primary amine 9. This amine (9) was treated with various sulfonyl chlorides (Procedure 9) to obtain sulfonamides 10–15.

Sulfonamide 11 was further transformed to 16 (Scheme 2) by hydrolysis of the nitrile with hydrogen peroxide to obtain carboxamide 16 (Tetrahed. Lett. 1989, 949).

Primary amine 9 was also converted into carboxamides 17 and 18 using the appropriate carboxylic acid chloride (Scheme 2).

Aryl bromide 7 was treated with t-butyllithium, followed by diphenylphosphorylazide, and then by sodium bis(2-methoxyethoxy)aluminum hydride (Scheme 2) to afford amine 19 (Tetrahed. Lett. 1984, 429). This amine was treated with sulfonyl chlorides to obtain sulfonamides 20 and 21.

Scheme 3: (Formula I Analogs)

Aminotetralin 22 (J. Org. Chem. 1995, 4324) was protected with a BOC-group and then subjected to metal-halogen exchange with t-butyllithium, followed by DMF quench to obtain an aldehyde. This aldehyde was reduced with sodium borohydride to obtain a benzylic alcohol. This was treated with thionyl chloride to obtain the benzylic chloride, which in turn was converted into the benzylic azide with sodium azide. Pd/C catalyzed hydrogenation of the azide afforded benzylic amine 24. This amine was condensed with various aryl sulfonyl chlorides to obtain the sulfonamides. These were treated with trifluoroacetic acid to remove the BOC-protecting groups (procedure 16), affording sulfonamide compounds 25–26. These were alkylated with bromopropane (procedure 17) to obtain the tertiary amine sulfonamides represented by 27.

Amine 24 was also condensed with aryl carboxylic acid chlorides to generate amides, which were then deprotected with trifluoroacetic acid to obtain amides 28–29. These amides (28–29) were heated with bromopropane (procedure 17) to generate the tertiary amine analogs, represented by 30.

Amine 24 was also condensed with aryl isocyanates to obtain ureas. These were deprotected with trifluoroacetic acid to generate ureas 31–33.

Scheme 4: (Formula I Analogs)

Diyne acid 34 (*J. Chem. Soc., Perkin Trans. I*, 1215–1224 (1986)) was induced to undergo a Curtius rearrangement with diphenylphosphoryl azide, trapping the isocyanate intermediate with t-butanol to obtain the BOC-protected product. The BOO-group was cleaved with trifluoroacetic acid to afford the primary amine, which was then treated with trifluoroacetic anhydride to obtain 35. This diyne (35) was treated with Wilkinson's catalyst and the 1,4-diacetoxy-2-butyne to afford 36 (*Tetrahed. Lett.*, 34, 23–26 (1993)). The acetates and trifluoroacetyl group were cleaved with base and the product alkylated with n-bromopropane to afford 37. This diol was treated with allylamine to give the 5-membered amine ring; subsequently the allyl group was removed with palladium catalysis to afford 38. Amine 38 was condensed with various arylsulfonyl chlorides (procedure 9) to afford sulfonamides 39–46.

Scheme 5: (Formula II Analogs)

Pyridone 47 (*J. Chem. Soc. Perkin Trans.* 1990, 195) was hydrolyzed (Scheme 5) with aqueous perchloric acid at 95° C. to obtain ketone 48. This ketone underwent reductive amination with n-propylamine using 50 p.s.i. hydrogenation gas and acetic acid and platinum oxide in ethanol. The propyl-substituted amine (49) was obtained in good yield. Treatment with di-t-butyl dicarbonate in THF afforded the BOC-protected compound (50). This was condensed with 4-chlorobenzenesulfonyl chloride in the presence of DMAP and triethylamine to give sulfonyloxy substituted pyridine 51. Deprotection of the BOC group with trifluoroacetic acid at 25° C. gave amine 52 after workup. This could be converted to the dipropylamine analog (53) by heating with n-bromopropane in acetonitrile in the presence of potassium carbonate.

Scheme 6: (Formula II Analogs)

Diyne 54, whose preparation is already described, was treated with N-benzyloxy-2-aminoacetonitile under the influence of cobalt catalysis (*J. Chem. Soc., Chem. Comm.*, 133–134 (1982)) to obtain heterocycle 55. The BOC-group was removed with trifluoroacetic acid and the amine was alkylated with n-bromopropane to afford 56. The CBZ-group was removed by palladium catalyzed hydrogenation to afford amine 57. This amine was treated with aryl sulfonyl chlorides (procedure 9) to obtain sulfonamides represented by 58–59.

Amine 57 was also treated with arylcarboxylic acid chlorides (procedure 11) to obtain amides represented by 60.

Amine 57 was also treated with aryl isocyanates (procedure 33) to obtain ureas represented by 61–62.

Scheme 7: (Formula III Analogs)

Ketone 63 (*Helv. Chim. Acta* 1994 1256) underwent reductive amination with sodium cyanoborohydride in the presence of acetic acid and propanal to afford 64. This amine was protected with a BOC-group and the compound was treated with n-butyllithium at low temperature followed by a quench with dimethylformamide to afford aldehyde 65. This aldehyde was condensed with hydroxylamine hydrochloride to obtain 66. Oxime 66 was reduced with Devarda's alloy (alloy of 50% copper, 45% aluminum, 5% zinc) to obtain amine 67. This amine was treated with 4-chlorophenylisocyanate to obtain urea 68.

Scheme 8: (Formula I Analogs)

The hydroxy,triflate 69 (Patent 4714) was alkylated with various alkyl halides using sodium hydride in DMF to afford the intermediates 70–73 (procedure 38). These triflate intermediates were converted via carbonylation using palladium acetate and 1,3-bis(diphenylphosphinopropane) under carbon monoxide atmosphere (procedure 39) to yield the methyl ester intermediates 74–77. These methyl esters intermediates were converted to either the primary carboxamide products 78–81 using formamide and sodium methoxide (procedure 40) or converted to the alkylcarboxamide products 82–84 using appropriate substituted formamides and sodium methoxide (procedure 41). The primary carboxamide 81 was further elaborated using sodium hydride and an alkyl halide (procedure 42) to the alkylcarboxamide product 85.

The hydroxy, ester 86 (patent 4714) was converted to the carboxamide 87 using sodium methoxide and formamide (procedure 43) followed by alkylation using potassium carbonate and alkyl halides (procedure 44) to give 88–90.

Scheme 9: (Formula I Analogs)

The dimethylester 91 (patent 4714) was hydroylzed to the dicarboxylic acid 92 using aqueous NaOH/MeOH (procedure 45). This diacid was then condensed and cyclized with ammonium acetate and HCl in acetic acid to give 93 (procedure 46) or alternatively condensed with various amines in acetic acid to give 95–124 (procedure 49). The products 93, 95–124 were reduced to the corresponding lactam derivatives 94, 125–133 with zinc/acetic acid (procedure 47). The intermediates 93 and 94 were also alkylated with various substituted halides to give 95–124 and 125–133 (procedure 48 and 50).

Scheme 10: (Formula I Analogs)

The dicarboxylic acid 92 was condensed with various hydrazines in acetic acid to give 134–135 (procedure 51).

The following procedures 1–9 from Scheme 1 are useful in the preparation of the Examples 1–6 of this invention (with the exception of Example 5 which was inactive in the dopamine screen).

Procedure 1: (R)-4-Bromo-α-[(methoxycarbonyl)amino]-γ-oxobenzenebutanoic acid. 2

A mixture of bromobenzene (373 g) and (R)-2-carbomethoxyaminosuccinic anhydride (1) (90.51 g) in dichloromethane (260 ml) was cooled in ice, and aluminum chloride (174.34 g) was added over 1 minute (exothermic!). The dark red mixture was stirred at 0° C. for 30 minutes and at room temperature for 1 hour. The mixture was poured onto crushed ice, and concentrated hydrochloric acid was added slowly with stirring. Diethylether was added and the mixture was stirred until all of the red-brown material disappeared. The layers were separated, and the aqueous was extracted twice more with diethylether. The combined ether extracts were washed with water and extracted with aqueous sodium carbonate. The combined extracts were washed with diethylether, cooled in ice, and acidified with conc. hydrochloric acid. The acid was extracted 3 times with diethylether. The combined extracts were washed with brine and dried ($MgSO_4$). The solvent was removed under vacuum to leave the title compound as a foam, 149.6 g. $[\alpha]_D=-41°$ (25° C., $CH_3OH$, c=1.0352).

Procedure 2: (R)-4-Bromo-α-[(methoxycarbonyl)amino] benzenebutanoic acid. 3

A solution of (R)-4-bromo-α-[(methoxycarbonyl)amino]-γ-oxobenzenebutanoic acid (2) (74.35 g) in dichloromethane and triethylsilane (182 ml) was cooled to 0° C. and titanium tetrachloride (99.0 ml) was added dropwise over a period of 15 minutes with stirring. After 5.5 hours, triethylsilane (72 ml) was added, and the mixture was stirred at room temperature for 17 hours and at reflux on the steam bath for 3 hours. The mixture was cooled and poured onto ice. The mixture was extracted twice with diethylether. The combined ether extracts were washed with water and extracted 3 times with 250 ml portions of 10% sodium carbonate solution. The combined extracts were washed with diethylether, cooled in ice, and acidified with concentrated hydrochloric acid. The precipitate was filtered, washed with water, and dried under vacuum to leave a white solid. Crystallization from ethyl acetate/hexane gave the title compound as white crystals (52.7 g, 74%, m.p. 136–137° C.). $[\alpha]_D$=−12° (25° C., $CH_3OH$, c=0.8709).

Procedure 3: Methyl (R)-(7-Bromo-1,2,3,4-tetrahydro-1-oxo-2-naphthalenyl)carbamate. 4

A suspension of (R)-4-bromo-α-[(methoxycarbonyl) amino]benzenebutanoic acid (3) (97.0 g) in dichloromethane was cooled in ice, and dimethyl formamide (1.2 ml) and oxalyl chloride (28.1 ml) were added. The mixture was stirred at 0° C. for 5 minutes and at room temperature for 1.5 hours. The solution was cooled to −25° C., and aluminum chloride (86.4 g) was added portionwise over 12 minutes. The mixture was stirred at −20° C. for 40 minutes and poured onto a mixture of ice, 10% hydrochloric acid (300 ml), and chloroform (100 ml) with stirring. The mixture was extracted twice with diethylether, and the extracts were washed with water, saturated sodium bicarbonate solution, and brine. The solution was dried ($MgSO_4$), and the solvent was removed under vacuum to leave a slightly yellow solid (91.76 g). Crystallization from methanol gave colorless crystals which were filtered, washed with hexane and dried under vacuum (69.9 g, 76% m.p. 116–117° C.). The filtrate was evaporated and the residue was recrystallized from methanol to give more of the title compound as an off-white solid (6.81 g, m.p. 111–112° C.). $[\alpha]_D$=+43° (25° C., $CH_3OH$, c=0.8143).

Procedure 4: Methyl (R)-(7-Bromo-1,2,3,4-tetrahydro-2-naphthalenyl)carbamate. 5

Into a 2l, 3-necked flask equipped with a mechanical stirrer, a 125 ml addition funnel, and a $N_2$ inlet was placed a solution of methyl (R)-(7-bromo-1,2,3,4-tetrahydro-1-oxo-2-naphthalenyl)carbamate (4) (68.74 g) in dichloromethane (147 ml) was added. Triethylsilane (147 ml) and the mixture was cooled in ice. Titanium tetrachloride (76.2 ml) was added via the addition funnel over a period of 10 minutes, and the mixture was stirred at room temperature for 24 hours. Triethylsilane (18.5 ml) was added, and the mixture was stirred for an additional 2 hours. The mixture was poured onto ice, the layers were separated, and the aqueous layer was extracted twice with dichloromethane. The combined extracts were washed twice with 5% hydrochloric acid, once with water, and once with 5% sodium hydroxide solution. The solution was dried ($MgSO_4$), and the solvent was removed under vacuum to leave an oil which partially crystallized (122.9 g). The mixture was diluted with hexane, cooled in ice, and filtered giving a white solid (60.88 g). Crystallization from ethyl acetate/hexane gave the title compound as colorless crystals (52.69 g, 0.185 mol, 80.3%, m.p. 99–100.5° C.). A second crop (5.29 g) was obtained. Chiral HPLC analysis: (Chiralcel OD column, Daicel Chem. Ind., LTD; 10% isopropanol in hexane; 1 ml/min flow rate; λ=215; 25 cm×4.6 mm id column) shows 3.26 min (1.5%), 8.57 min (1.7%), 10.66 min (96.9%), 13.97 min (1.6%). The racemate shows 3.27 min (1.2%), 8.66 min (0.3%), 10.75 min (48.9%), 14.30 min (49.4%), 25.79 min (0.2%). $[\alpha]_D$=+74° (25° C., $CH_3OH$, c=0.8884).

Procedure 5: (R)-7-Bromo-1,2,3,4-tetrahydro-2-naphthalenamine (Z)-2-butenedioate (1:1). 6

Methyl (R)-(7-bromo-1,2,3,4-tetrahydro-2-naphthalenyl) carbamate (5) (51.62 g), potassium hydroxide (61.2 g), water (150 ml) and ethanol (350 ml) were heated at reflux for two days. The ethanol was removed under vacuum, and the residue was partitioned between water and 2:1 diethylether/tetrahydrofuran. The aqueous layer was extracted again with the same solvent, and the combined extracts were washed with brine and dried ($MgSO_4$). The solvent was removed under vacuum to leave an oil (37.9 g). A sample of the compound (15.28 g) was combined with maleic acid (7.85 g), and the mixture was crystallized from methanol/diethylether to give the title compound as colorless crystals (19.24 g, m.p. 184–184.5° C.). $[\alpha]_D$=+40° (25° C., $CH_3OH$, c=0.7756). A second crop (2.05 g) was obtained.

Procedure 6: (R)-7-Bromo-1,2,3,4-tetrahydro-N,N-dipropyl-2-naphthalenamine 4-Methylbenzenesulfonate. 7

A mixture of (R)-2-amino-3-bromo-1,2,3,4-tetrahydronaphthalene (6) (22.62 g), 1-bromopropane (36.4 ml), and potassium carbonate (41.5 g) in acetonitrile was stirred at reflux for 16 hours. 1-Bromopropane (20 ml was added, and the reflux was continued for 8 hours. The mixture was partitioned between water and diethylether. The aqueous layer was extracted again with diethylether, and the combined ether extracts were washed with brine and dried ($MgSO_4$). The solvent was removed under vacuum to leave an oil (29.18 g). Purification by flash chromatography (230–400 mesh silica gel, ethyl acetate/hexane) gave an oil (26.4 g, 85%). A sample (0.997 g) was combined with p-toluenesulfonic acid hydrate (0.62 g), and crystallized from methanol/diethylether to give the title compound as colorless crystals (1.39 g, m.p. 182–183.5° C.). $[\alpha]_D$=+48° (25° C., $CH_3OH$, c=0.9834).

Procedure 7: (R)-7-(Dipropylamino)-5,6,7,8-tetrahydro-2-naphthalenecarboxamide. 8

A solution of (R)-2-(dipropylamino)-7-bromo-1,2,3,4-tetrahydronaphthalene (7) (13.02 g) in dry tetrahydrofuran was cooled to −78° C. t-Butyllithium (1.7 M in pentane, 50.6 ml) was added via syringe over a period of 6 minutes, and the mixture was stirred for an additional 8 minutes. Trimethylsilylisocyanate (13.4 ml, 85% pure, 84.1 mmol) was added in one dose, and the mixture stirred at −78° C. for 10 minutes and at room temperature for 1.5 hours. The reaction mixture was quenched with 10% hydrochloric acid, and after stirring for 30 minutes, it was basified with 15% sodium hydroxide. The free base was extracted with diethylether and 1:1 tetrahydrofuran/diethylether. The combined extracts were washed with brine and dried ($MgSO_4$). The solvent was removed under vacuum to leave an oil (15.25 g). Crystallization from ethyl acetate/hexane gave off-white crystals (6.30 g), m.p. 132–132° C. $[\alpha]_D$=+67° (25° C., $CH_3OH$, c=0.8139).

Procedure 8: (R)-7-(Dipropylamino)-5,6,7,8-tetrahydro-2-naphthalenemethanamine. 9

A solution of the (R)-7-(dipropylamino)-5,6,7,8-tetrahydro-2-naphthalenecarboxamide (8) (8.68 g) in dry tetrahydrofuran was stirred at room temperature and borane dimethylsulfide complex (10.0 M, 11.1 ml) was slowly added. When the initial reaction subsided, the mixture was heated at reflux for 2 days. The mixture was cooled in ice, and water was added dropwise. When the evolution of gas ceased, 10% hydrochloric acid (75 ml) was added, and the mixture was refluxed for 2 hours. The mixture was cooled in ice and basified with solid sodium hydroxide. The mixture was extracted with diethylether and then with 2:1 diethylether/tetrahydrofuran. The combined extracts were washed with brine and dried ($MgSO_4$). The solvent was removed under vacuum to leave the title compound a yellow oil (8.15 g) which was used without further purification.

EXAMPLE 1

Procedure 9: (R)-N-[[7-(Dipropylamino)-5,6,7,8-tetrahydro-2-naphthalenyl]methyl]methanesulfonamide. 10

A solution of crude (R)-7-(dipropylamino)-5,6,7,8-tetrahydro-2-naphthalenemethanamine (9) (0.521 g) and triethylamine (0.30 ml) in tetrahydrofuran was cooled to 0° C. Methanesulfonyl chloride (0.16 ml) was added dropwise with stirring. The mixture was stirred at room temperature for 1.5 hours and quenched with 10% sodium carbonate solution. The mixture was extracted twice with diethylether and the combined extracts were washed with brine and dried (MgSO$_4$). The solvent was removed under vacuum to leave an oil (0.63 g). Purification by flash chromatography (ethyl acetate/hexane) gave the title compound as a colorless oil (0.47 g). [α]$_D$=+58° (25° C., CH$_3$OH, c=0.5221).

EXAMPLE 2

(R)-4–Cyano-N-[[7-(dipropylamino)-5,6,7,8-tetrahydro-2-naphthalenyl]methyl]benzenesulfonamide. 11

Using procedure 9, a solution of crude (R)-7-(dipropylamino)-5,6,7,8-tetrahydro-2-naphthalenemethanamine (9) was treated with 4-cyanophenylsulfonyl chloride. Purification by chromatography gave a sample which was crystallized from ethyl acetate/hexane to give 11 as colorless crystals (m.p. 94–95.5° C.). [α]$_D$=+46° (25° C., CH$_3$OH, c=0.7967).

EXAMPLE 3

(R)-4-Chloro-N-[[7-(dipropylamino)-5,6,7,8-tetrahydro-2-naphthalenyl]methyl]benzenesulfonamide. 12

Using procedure 9, (R)-7-(dipropylamino)-5,6,7,8-tetrahydro-2-naphthalenemethanamine (9) was treated with 4-chlorobenzenesulfonyl chloride. Purification by chromatography gave a solid which was crystallized from hexane to give the title compound colorless crystals (m.p. 72° C.). [α]$_D$=+47° (25° C., CH$_3$OH, c=0.6095).

EXAMPLE 4

(R)-4-Nitro-N-[[7-(dipropylamino)-5,6,7,8-tetrahydro-2-naphthalenyl]methyl]benzenesulfonamide. 13

Using procedure 9, (R)-7-(dipropylamino)-5,6,7,8-tetrahydro-2-naphthalenemethanamine 9 and triethylamine in dry tetrahydrofuran was cooled to 0° C., and 4-nitrobenzenesulfonyl chloride was added. After extraction, purification by flash chromatography (ethyl acetate/hexane) gave a solid which was crystallized from hexane containing a small amount of ethyl acetate to give 13 as yellow crystals (m.p.105° C.). [α]$_D$=+49° (25° C., CH$_3$OH, c=0.9425).

EXAMPLE 5

(R)-3–Cyano-N-[[7-(dipropylamino)-5,6,7,8-tetrahydro-2-naphthalenyl]methyl]benzenesulfonamide.14
(Inactive in Dopamine Screen)

Using procedure 9, (R)-7-(dipropylamino)-5,6,7,8-tetrahydro-2-naphthalenemethanamine 9 and triethylamine in dry tetrahydrofuran was cooled to 0° C., and 3-cyanobenzenesulfonyl chloride was added. After extraction, purification by flash chromatography (ethyl acetate/hexane) gave the title compound as an oil. [α]$_D$=+41° (25° C., CH$_3$OH, c=1.0394).

EXAMPLE 6

(R)-N-[[7-(Dipropylamino)-5,6,7,8-tetrahydro-2-naphthalenyl]methyl]1-methyl-1H-imidazole-4-sulfonamide. 15

Using procedure 9, (R)-7-(dipropylamino)-5,6,7,8-tetrahydro-2-naphthalenemethanamine 9 and triethylamine in dry tetrahydrofuran was cooled to 15° C., and 1-methylimidazole-4-sulfonyl chloride was added. After extraction, purification by flash chromatography (tetrahydrofuran/ethyl acetate) gave the title compound as an oil. [α]$_D$=+46° (25° C., CH$_3$OH, c=0.7458).

EXAMPLE 7

Procedure 10. (R)-Carboxamido-N-[[7-(dipropylamino)-5,6,7,8-tetrahydro-2-naphthalenyl]methyl]benzenesulfonamide. 16

(R)-4–Cyano-N-[[7-(dipropylamino)-5,6,7,8-tetrahydro-2-naphthalenyl]methyl]benzenesulfonamide (11) was treated with hydrogen peroxide and sodium hydroxide in aqueous THF. After completion of the hydrolysis the solution was extracted with ether/water. The ether layer was dried over sodium sulfate and the solvent removed. The residue was chromatographed with ethyl acetate/hexane to afford 16 as a solid.

EXAMPLE 8

Procedure 11. (R)-4Chloro-N-[[7-(dipropylamino)-5,6,7,8-tetrahydro-2-naphthalenyl]methyl]benzamide. 17

(R)-7-(dipropylamino)-5,6,7,8-tetrahydro-2-naphthalenemethanamine 9 (0.521 g) and triethylamine (0.30 ml) in tetrahydrofuran (6 ml) were cooled to 0° C., and 4-chlorobenzoyl chloride (0.254 ml) was added. The mixture was allowed to warm to room temperature and was stirred for 3 hours. The reaction was quenched with 10% sodium carbonate solution, and the mixture was stirred for 30 minutes. The mixture was extracted twice with 1:1 tetrahydrofuran/diethylether, and the combined organics were washed with brine and dried (MgSO$_4$). The solvent was removed under vacuum to leave a solid which was crystallized from ethyl acetate to give the title compound as colorless crystals (0.52 g, m.p. 209.5° C.). [α]$_D$=+42° (25° C., CHCl$_3$, c=0.9118).

EXAMPLE 9

(R)-4-Cyano-N-[[7-(dipropylamino)-5,6,7,8-tetrahydro-2-naphthalenyl]methyl]benzamide. 18
(A Comparison Example for this Invention)

Using procedure 11, (R)-2-(dipropylamino)-7-amino-1,2,3,4-tetrahydronaphthalene 9 and triethylamine in tetrahydrofuran were cooled to 0° C., and 4-cyanobenzoyl chloride was added. After extraction, etc., the solid was crystallized from ethyl acetate to give the title compound as off-white crystals (m.p.183° C.). [α]$_D$=+50° (25° C., CH$_3$OH, c=0.9773).

Procedure 12. (R)-2-(Dipropylamino)-7-amino-1,2,3,4-tetrahydronaphthalene. 19

(R)-2-(Dipropylamino)-7-bromo-1,2,3,4-tetrahydronaphthalene 7 (5.91 g) was dissolved in dry tetrahydrofuran (50 ml) under nitrogen and cooled to −78° C. t-Butyllithium (1.7 M in pentane, 23.0 ml) was added over 5 minutes, and the mixture was stirred at −78° C. for an additional 10 minutes. This solution was added via needle-stock to a solution of diphenylphosphoryl azide (5.24 g) in tetrahydrofuran (30 ml) over a 10 minute period. The mixture was stirred at −78° C. for 2 hours and was warmed to −20° C. over 45 minutes. The mixture was again cooled to −78° C., and sodium bis(2-methoxyethoxy)aluminum hydride (3.4 M in toluene, 22.4 ml) was added over 5 minutes. After stirring at −78° C. for an additional 10 minutes, the mixture was warmed to 0° C. and stirred for 45 minutes and at room temperature for 30 minutes. The mixture was carefully quenched with water, and saturated with sodium chloride. The amine was extracted twice with diethylether, and the combined extracts were dried (MgSO$_4$). The solvent was removed under vacuum to leave an oil (6.3 g). Purification by flash chromatography gave the 19 as a light amber oil (2.56 g).

EXAMPLE 10
Procedure 13. (R)-4-Chloro-N-[7-(dipropylamino)-5,6,7,8-tetrahydro-2-naphthalenyl]benzenesulfonamide 20 p-Chlorobenzenesulfonyl chloride (0.32 g) was added to a solution of (R)-2-(dipropylamino)-7-amino-1,2,3,4-tetrahydronaphthalene 19 (0.370 g) and triethylamine (0.30 ml) in dry tetrahydrofuran (4 ml). The mixture was stirred at room temperature overnight. The reaction was quenched with 10% sodium carbonate solution (5 ml), and the mixture was stirred for 10 minutes. The mixture was extracted twice with diethylether, and the combined extracts were washed with brine and dried (MgSO$_4$). The solvent was removed under vacuum to leave an oil (0.63 g). Purification by flash chromatography (ethyl acetate in hexane) gave 20 as an amber oil. $[\alpha]_D$=+52° (25° C., CH$_3$OH, c=1.0535).

EXAMPLE 11
(R)-4-Cyano-N-[7-(dipropylamino)-5,6,7,8-tetrahydro-2-naphthalenyl]benzenesulfonamide. 21

Using procedure 13, p-cyanobenzenesulfonyl chloride was added to a solution of crude (R)-2-(dipropylamino)-7-amino-1,2,3,4-tetrahydronaphthalene 19 and triethylamine in dry tetrahydrofuran. After extraction, etc., purification by flash chromatography (ethyl acetate in hexane) gave 21 as an amber oil which could be crystallized as its fumarate salt from methanol/ether (m.p. 123° C. dec). $[\alpha]_D$=+48° (25° C., CH$_3$OH, c=1.0113).

Procedure 14: tert-Butyl (R)-(6-bromo-1,2,3,4-tetrahydro-N-propyl-2-naphthaleneamine)carbamate. 23

Propionyl chloride (18.5 ml) was added to (R)-2-amino-7-bromo-1,2,3,4-tetrahydronaphthalene (22) (*J. Org. Chem.* 1995, 4324) (43 g), triethylamine (31 ml) and dichloromethane. After 2 hours, the volume was concentrated under vacuum; THF was added and concentrated under vacuum again. Water was added, cooled in an ice bath, and the solid filtered. Washing with water and drying under vacuum provided 51 g of a solid, m.p. 169–171° C. Borane dimethylsulfide complex (27 ml, 10M) was refluxed with this amide (51 g) in THF for 24 hours. Water was added, then 2 N hydrochloric acid. This was refluxed for an hour and was then basified with 15% aqueous sodium hydroxide and extracted with methyl t-butylether. The ether layer was washed with water and brine, and was dried with sodium sulfate. Solvent was removed under vacuum to give 48 g of a dark oil. This amine and ditert-butyl dicarbonate (44 g) were combined in THF. After 60 minutes, water (150 ml) was added and a catalytic amount of 4-dimethylaminopyridine. After 15 hours it was partitioned between water and methyl t-butylether. The ether layer was washed with 2N hydrochloric acid, water, saturated aqueous sodium bicarbonate, and brine, and was dried with sodium sulfate. Solvent was removed under vacuum, and crystallization from hexane provided 59 g of 23 as a solid, m.p. 67–69° C.

Procedure 15: tert-Butyl (R)-(6-aminomethyl-1,2,3,4-tetrahydro-N-propyl-2-naphthaleneamine)carbamate. 24 tert-Butyllithium (1.7 M in pentane) (64 ml) was added to tert-butyl (R)-(6-bromo-1,2,3,4-tetrahydro-N-propyl-2-naphthaleneamine)carbamate (23) (20 g) in dry THF (125 ml) at −78° C. After 10 minutes, dry N,N-dimethylformamide (8 ml) was added and the cold bath removed. After 90 minutes, the solution was partitioned between water and ether. The ether layer was washed with water and brine and was dried over sodium sulfate. Solvent was removed under vacuum to give 17 g of a solid, m.p. 88–91° C. Sodium borohydride (1.7 g) was added in portions to this aldehyde (14 g) in methanol in an ice bath. After 2 hours, water was added and the solution concentrated under vacuum. The residue was partitioned between water and ether. The ether layer was washed with water and brine and was dried with sodium sulfate. Solvent was removed under vacuum to give 14 g of the benzylic alcohol as a solid, m.p. 113–114° C. $[\alpha]_D$=+53° (25° C., CH$_3$OH, c=0.96). Thionyl chloride (3.3 ml) was added slowly to this benzylic alcohol (13.6 g) in THF at 0° and then the ice bath was removed. After an hour, aqueous sodium bicarbonate was added and it was extracted with ether. The ether layer was washed with water and brine and was dried with sodium sulfate. Solvent was removed under vacuum and the residue was chromatographed on silica gel with dichloromethane/hexane to give 9.6 g of the benzylic chloride as a solid, m.p. 90–93° C. $[\alpha]_D$=+50° (25° C., CH$_3$OH, c=0.94). Sodim azide (8.7 g) and the benzylic chloride (9.0 g) were heated at 45° C. in DMF for 18 hours, and then partitioned between ether/THF and water. The ether layer was washed with water and brine and was dried with sodium sulfate. Solvent was removed under vacuum to give 9.2 g of the azide as a solid, m.p. 73.5–75.0° C. $[\alpha]_D$=+50° (25° C., CH$_3$OH, c=1.00). The azide (9.1 g) and palladium on carbon (0.5 g) were shaken in THF under 45 PSI hydrogen for 3 hours. The mixture was filtered through diatomaceous earth and solvent was removed under vacuum to give 7.9 g of 24 as a solid. An analytical sample was crystallized from hexane, m.p. 88–89° C. $[\alpha]_D$=+53° (25° C., CH$_3$OH, c=1.00).

EXAMPLE 12
Procedure 16; (R)-4-Chloro-N-[[5,6,7,8-tetrahydro-6-(propylamino)-2-naphthalenyl]methyl]benzenesulfonamide. 25 tert-Butyl (R)-(6-aminomethyl-1,2,3,4-tetrahydro-N-propyl-2-naphthaleneamine)carbamate (24) (0.50 g), triethylamine (0.44 ml), 4-chlorobenzenesulfonyl chloride (0.36 g) and THF were stirred for 3 hours. The mixture was partitioned between aqueous sodium bicarbonate and ether/THF. The ether layer was washed with brine and dried with sodium sulfate. Solvent was removed and the residue was chromatographed on silica gel (dichloromethane/ethyl acetate/hexane) to give 0.77 g of a solid, m.p.117–121 ° C. $[\alpha]_D$=+32° (25° C., CH$_3$OH, c=0.78). To remove the BOC-protecting group, this solid was stirred with trifluoroacetic acid (5 ml) for 90 minutes and solvent was removed under vacuum. The mixture was partitioned between aqueous sodium bicarbonate and ether/THF. The ether layer was washed with brine and dried with sodium sulfate. Solvent was removed and gave 0.53 g of crystalline 25, m.p. 145–147° C.

EXAMPLE 13
(R)-4-[3,5-Dimethyl-N-[[5,6,7,8-tetrahydro-6-(propylamino)-2-naphthalenyl]methyl]]isoxazolesulfonamide. 26

Using procedure 16, tert-butyl (R)-(6-aminomethyl-1,2,3,4-tetrahydro-N-propyl-2-naphthaleneamine)carbamate (24) was treated with 3,5-dimethylisoxazole sulfonyl chloride to give crystalline 26 as its trifluoroacetic acid salt after deprotection of the BOC-group.

EXAMPLE 14
Procedure 17. (R)-4-Chloro-N-[[5,6,7,8-tetrahydro-6-(dipropylamino)-2-naphthalenyl]methyl]benzenesulfonamide. 27

Sodium triacetoxyborohydride (0.20 g) was added to (R)-4-chloro-N-[[5,6,7,8-tetrahydro-6-(propylamino)-2-naphthalenyl]methyl]benzenesulfonamide (25) (0.29 g), propionaldehyde (0.07 ml), glacial acetic acid (0.05 ml), and dichloromethane. After 3.5 hours, the mixture was partitioned between aqueous sodium bicarbonate and ether/THF. The ether layer was washed with water and brine and was dried with sodium sulfate. Solvent was removed under vacuum to give 0.31 g of 27 as a solid, m.p. 101–103° C. $[\alpha]_D$=+42° (25° C., CH$_3$OH, c=0.93).

EXAMPLE 15
Procedure 18. (R)-4-Chloro-N-[[5,6,7,8-tetrahydro-6-(propylamino)-2-naphthalenyl]methyl]benzamide. 28 tert-Butyl (R)-(6-aminomethyl-1,2,3,4-tetrahydro-N-propyl-2-naphthaleneamine)carbamate (24) (0.50 g), triethylamine (0.44 ml), 4-chlorobenzoyl chloride (0.21 ml) and THF were stirred for 2.5 hours. The mixture was partitioned between aqueous sodium bicarbonate and ether/THF. The ether layer was washed with brine and dried with sodium sulfate. Solvent was removed and the residue was chromatographed on silica gel (dichloromethane/ethyl acetate/hexane) to give 0.56 g of a solid, m.p. 154–155° C. $[\alpha]_D$=+38° (25° C., CH$_3$OH, c=0.86). To remove the BOC-protecting group, this solid was stirred with trifluoroacetic acid (5 ml) for 60 minutes and the solvent was removed under vacuum. The residue was partitioned between aqueous sodium bicarbonate and ether/THF. The ether layer was washed with water and then dried with sodium sulfate. Solvent was removed under vacuum to give 0.34 g of 28 as a solid, m.p. 147–148° C. $[\alpha]_D$=+49° (25° C., CH$_3$OH, c=0.87).

EXAMPLE 16
(R)-2-Acetyl-N-[[5,6,7,8-tetrahydro-6-(dipropylamino)-2-naphthalenyl]methyl]benzamide. 29

Using procedure 18, tert-Butyl (R)-(6-aminomethyl-1,2,3,4-tetrahydro-N-propyl-2-naphthaleneamine)carbamate (24) (0.3 g) can be treated with an appropriate amount of 2-acetyl benzoyl chloride to give a white solid, m.p. 99° C. $[\alpha]_D$=+35° (25° C., CH$_3$OH, c=0.95). This was stirred with trifluoroacetic acid (5 ml) for 90 minutes and solvent was removed under vacuum. Trituration with dry diethyl ether gave 0.28 g of crystalline 29 as its trifluoroacetic acid salt, m.p. 153–156° C. $[\alpha]_D$=+45° (25° C., CH$_3$OH, c=0.86).

EXAMPLE 17
(R)-4-Chloro-N-[[5,6,7,8-tetrahydro-6-(dipropylamino)-2-naphthalenyl]methyl]benzamide. 30

Using procedure 17, (R)-4-chloro-N-[[5,6,7,8-tetrahydro-6-(propylamino)-2-naphthalenyl]methyl]benzamide (28) was converted to 30 as a solid, m.p. 141–142° C. $[\alpha]_D$=+43° (25° C., CH$_3$OH, c=0.90).

EXAMPLE 18
Procedure 19. (R)-N-(4-Acetylphenyl)-N'-[[5,6,7,8-tetrahydro-6-(propylamino)-2-naphthalenyl]methyl]urea. 31 tert-Butyl (R)-(6-aminomethyl-1,2,3,4-tetrahydro-N-propyl-2-naphthaleneamine)carbamate (24) (0.30 g), 4-acetylphenyl isocyanate (0.16 g) and THF were stirred for 6 hours. It was partitioned between aqueous sodium bicarbonate and ether/THF. The ether layer was washed with brine and dried with sodium sulfate. Solvent was removed and the residue was chromatographed on silica gel (dichloromethane/ethyl acetate/hexane) to give 0.35 g of a solid, m.p. 77–88° C. $[\alpha]_D$=+34° (25° C., CH$_3$OH, c=0.83). This was stirred with trifluoroacetic acid (5 ml) for 90 minutes and solvent was removed under vacuum. Trituration with dry diethyl ether gave 0.30 g of crystalline 31 as its trifluoroacetic acid salt, m.p. 200° C. (decomposition).

EXAMPLE 19
(R)-N-(4-Chlorophenyl)-N'-[[5,6,7,8-tetrahydro-6-(propylamino)-2-naphthalenyl]methyl]urea. 32

Using procedure 19, tert-butyl (R)-(6-aminomethyl-1,2,3,4-tetrahydro-N-propyl-2-naphthaleneamine)carbamate (24) (0.70 g) was treated with 4-chlorophenyl isocyanate (0.36 g), then with trifluoroacetic acid to give 0.59 g of crystalline 32 as its trifluoroacetic acid salt, m.p. 192° C. (decomposition).

EXAMPLE 20
(R)-N-(4-Nitrophenyl)-N'-[[5,6,7,8-tetrahydro-6-(propylamnino)-2-naphthalenyl]methyl]urea. 33

Using procedure 19, tert-butyl (R)-(6-aminomethyl-1,2,3,4-tetrahydro-N-propyl-2-naphthaleneamine)carbamate (24) (0.30 g) was treated with 4-nitrophenyl isocyanate (0.17 g), then with trifluoroacetic acid followed by basification and extraction to give 33 as a solid.

Procedure 20: 4-(trifluoroacetylamino)heptan-1,6-diyne. 35

Triethylamine (19.5 g, 0.193 mol) was added to a solution of 2-(propyn-2-yl)-4-pentynoic acid (34, 25.0 g, 0.184 mol; *J. Chem. Soc., Perkin Trans. I*, 1215–1224 (1986)) in toluene (200 ml) with cooling. Diphenylphosphoryl azide (50.3 g, 0.184 mol) was added, and the mixture was stirred at room temperature for 15 minutes and heated on the steam bath until the evolution of gas ceased. Dry t-butanol (150 ml) was added, and the mixture was heated on the steam bath for 24 hours. The solvent was removed under vacuum, and the mixture was diluted with water and extracted twice with diethylether. The combined extracts were washed twice with 10% sodium carbonate solution and once with brine. The solution was dried (MgSO$_4$), and the solvent was removed under vacuum to leave a solid. Purification by flash chromatography on silica gel eluting with ethyl acetate/hexane gave a white solid which was crystallized from hexane to give 4-(t-butyloxycarbonylamino)heptan-1,6-diyne as colorless crystals (m.p. 64–67° C.).

4-(t-Butyloxycarbonylamino)heptan-1,6-diyne (30.0 g, 0.145 mol) was cooled in ice and trifluoroacetic acid (80 ml) was added. A vigorous evolution of gas ensued. The mixture was stirred at room temperature for 30 minutes and excess trifluoroacetic acid was removed under vacuum. The residue was partitioned between diethylether and water, and the aqueous layer was extracted with 10% hydrochloric acid. The combined aqueous extracts were cooled in ice and basified with solid sodium hydroxide and saturated with sodium chloride. The free base was extracted three times with diethylether. The combined extracts were washed with brine and dried (MgSO$_4$). The solvent was removed under vacuum to leave 4-aminoheptan-1,6-diyne as a light pink oil.

A solution 4-aminoheptan-1,6-diyne (14.63 g, 0.137 mol) and triethylamine (20.8 g, 0.206 mol) in dry tetrahydrofuran (100 ml) was cooled in ice and trifluoroacetic anhydride (37.5 g, 0.178 mol) was added with stirring over a 30 minute period. The mixture was stirred at 0° C. for 1 hour and then allowed to stand at −15° C. overnight. The mixture was stirred in an ice bath, and water (100 ml) was added dropwise. The layers were separated, and the aqueous was extracted with diethylether. The combined organic extracts were washed with 10% hydrochloric acid, saturated sodium bicarbonate solution (2×) and with brine. The solution was dried (MgSO$_4$), and the solvent was removed under vacuum to leave a solid. Crystallization from hexane/ethyl acetate gave 35 as slightly yellow crystals (m.p. 55–57° C.).

Procedure 21: N-[5,6-Bis(acetyloxy)methyl]-2,3-dihydro-1H-inden-2-yl]-2,2,2-trifluoroacetamide. 36

According to the procedure of Magnus et al. (*Tetrahed. Lett.*, 34, 23–26 (1993)), a solution of 2-butyn-1,4-diol diacetate (34.03 g, 0.200 mol; *Syn. Comm.*, 9, 789–797 (1979)) and tris(triphenylphosphine)rhodium chloride (2.78 g, 3.00 mmol) in argon degassed absolute ethanol (100 ml)

was heated to reflux and a solution of 4-(trifluoroacetylamino)heptan-1,6-diyne (35, 20.32 g, 0.100 mol) in argon degassed absolute ethanol (70 ml) was added via a syringe pump over a period of 2.5 hours. The mixture was stirred under argon at 75–80° C. for 8 hours and then at room temperature for 10 hours, and the solvent was removed under vacuum to leave a dark oil. Purification by flash chromatography on silica gel eluting with ethyl acetate/hexane gave a light amber solid. Crystallization from ethyl acetate/hexane gave 36 as tan crystals (m.p. 98–100° C.).

Procedure 22: 2-(dipropylamino)-5,6-bis(hydroxylmethyl) indane. 37

Potassium hydroxide (10.10 g, 0.180 mol) in water (35 ml) was added to a solution of N-[5,6-bis(acetyloxy)methyl]-2,3-dihydro-1H-inden-2-yl]-2,2,2-trifluoroacetamide (36, 20.1 g, 53.8 mmol) in methanol (200 ml) and heated to reflux for 2.5 hours. The solvent was removed under vacuum to leave a semi-solid. 1-Bromopropane (27.1 g, 0.220 mol), potassium carbonate (22.32 g, 0.162 mol), and acetonitrile (100 ml) were added, and the mixture was stirred at reflux on the steam bath for 17 hours. 1-Bromopropane (6.8 g, 0.055 mol) was again added, and the reflux was continued for 4 hours. The mixture was diluted with ethyl acetate and washed with water and brine, and the solution was dried ($MgSO_4$). The solvent was removed under vacuum to leave a brown oil. Purification by flash chromatography on silica gel eluting with tetrahydrofuran/ethyl acetate gave a solid. Crystallization from ethyl acetate/hexane gave 37 as white crystals (m.p. 111–113° C.).

Procedure 23: 1,2,3,5,6,7-Hexahydro-N,N-dipropylcyclopent[f]isoindol-6-armine. 38

Thionyl chloride (20 ml) was added to 2-(dipropylamino)-5,6-bis(hydroxylmethyl)indane (37, 5.55 g, 20.0 mmol) with stirring, and the mixture was refluxed on the steam bath for 1.75 hours. Excess thionyl chloride was removed under vacuum. The residue was dissolved in chloroform and the solvent was removed under vacuum. This process was repeated giving an amber solid. Crystallization from methanol/diethylether gave 2-(dipropylamino)-5,6-bis(chloromethyl)indane hydrochloride as off-white crystals (m.p. 208–210° C.).

Allylamine (9.3 g, 0.16 mol) was added to 2-(dipropylamino)-5,6-bis(chloromethyl)indane (3.41 g, 10.9 mmol) with stirring. An exothermic reaction ensued which was controlled with a cool water bath. The mixture was stirred at room temperature for 18 hours and then refluxed on the steam bath for 4 hours. Excess allylamine was removed under vacuum, and the residue was diluted with 10% sodium carbonate solution and extracted twice with diethylether. The combined extracts were washed with brine and dried ($MgSO_4$). The solvent was removed under vacuum to leave an amber oil. Purification by flash chromatography on silica gel eluting with tetrahydrofuran/ethyl acetate gave 2-(propen-2-yl)-1,2,3,5,6,7-hexahydro-N,N-dipropylcyclopent[f]isoindol-6-amine as an amber oil.

A mixture of the 2-(propen-2-yl)-1,2,3,5,6,7-hexahydro-N,N-dipropylcyclopent[f]isoindol-6-amine (7.9 g, 26.5 mmol), N,N'-dimethylbarbituric acid (12.41 g, 79.5 mmol), palladium acetate (0.297 g, 1.32 mmol), and triphenylphosphine (0.695 g, 2.65 mmol) in dichloromethane (75 ml) was degassed with argon and heated to 40° C. for 5 hours. The solvent was removed under vacuum, the residue diluted with 10% sodium carbonate solution, and extracted twice with diethylether. The combined extracts were washed with 10% sodium carbonate and extracted twice with 10% hydrochoric acid solution. An emulsion formed which was cleared by diluting with water and filtering through diatomaceous earth. The combined extracts were washed with diethylether and basified with solid sodium hydroxide. The free base was extracted three times with diethylether. The combined extracts were washed with brine and dried ($Na_2SO_4$). The solvent was removed under vacuum to leave 38 a brown solid, which could be crystallized with p-toluenesulfonic acid hydrate to give a gray-brown salt (m.p. 190–193° C.).

EXAMPLE 21

2-[(4-Chlorophenyl)sulfonyl]-1,2,3,5,6,7-hexahydro-N,N-dipropylcyclopent[f]isoindol-6-amine. 39

Using procedure 9, crude 1,2,3,5,6,7-hexahydro-N,N-dipropylcyclopent[f]isoindol-6-amine (38, 0.42 g, 1.6 mmol) was treated with 4-chlorobenzenesulfonyl chloride (0.343 g, 1.63 mmol). Purification by flash chromatography on silica gel using ethyl acetate/hexane and subsequent crystallization from methanol gave 39 as white crystals (m.p. 152–153° C.).

EXAMPLE 22

2-[(2-Chlorophenyl)sulfonyl]-1,2,3,5,6,7-hexahydro-N,N-dipropylcyclopent[f]isoindol-6-amine. 40

Using procedure 9, crude 1,2,3,5,6,7-hexahydro-N,N-dipropylcyclopent[f]isoindol-6-amine (38, 0.40 g, 1.5 mmol) was treated with 2-chlorobenzenesulfonyl chloride (0.36 g, 1.7 mmol). Purification by flash chromatography on silica gel using ethyl acetate/hexane and crystallization from methanol gave 40 as tan crystals (m.p. 89–91° C.).

EXAMPLE 23

2-[(3-Chlorophenyl)sulfonyl]-1,2,3,5,6,7-hexahydro-N,N-dipropylcyclopent[f]isoindol-6-amine. 41

Using procedure 9, crude 1,2,3,5,6,7-hexahydro-N,N-dipropylcyclopent[f]isoindol-6-amine (38, 0.60 g, 2.3 mmol) was treated with 3-chlorobenzenesulfonyl chloride (0.54 g, 2.6 mmol). Purification by flash chromatography on silica gel using ethyl acetate in hexane and crystallization from methanol gave 41 as tan crystals (m.p. 113–114 ° C.).

EXAMPLE 24

2-[(3-Cyanophenyl)sulfonyl]-1,2,3,5,6,7-hexahydro-N,N-dipropylcyclopent[f]isoindol-6-amine. 42

Using procedure 9, crude 1,2,3,5,6,7-hexahydro-N,N-dipropylcyclopent[f]isoindol-6-amine (38, 0.40 g, 1.5 mmol) was treated with 3-cyanobenzenesulfonyl chloride (0.35 g, 1.7 mmol). Purification by flash chromatography on silica gel using ethyl acetate in hexane and crystallization from methanol gave 42 as tan crystals (m.p. 134–135° C.).

EXAMPLE 25

2-[3,5-Dimethylisoxazolyl)-4-sulfonyl]-1,2,3,5,6,7-hexahydro-N,N-dipropylcyclopent[f]isoindol-6-amine. 43

Using procedure 9, 1,2,3,5,6,7-hexahydro-N,N-dipropylcyclopent[f]isoindol-6-amine (38) was treated with 3,5-dimethylisozazole-4-sulfonyl chloride. Crystallization from methanol gave 43 as gray crystals (m.p. 113–114 ° C.).

EXAMPLE 26

2-[(Benzofurazan)-4-sulfonyl]-1,2,3,5,6,7-hexahydro-N,N-dipropylcyclopent[f]isoindol-6-amine. 44

Using procedure 9, 1,2,3,5,6,7-hexahydro-N,N-dipropylcyclopent[f]isoindol-6-amine (38) was treated with benzofurazan-4-sulfonyl chloride. Crystallization from methanol gave 44 as gray-brown crystals (m.p. 115–118° C.).

EXAMPLE 27

2-{[2-(Benzoylaminomethyl)thiophene]-5-sulfonyl}-1,2,3,5,6,7-hexahydro-N,N-dipropylcyclopent[f]isoindol-6-amine. 45

Using procedure 9, 1,2,3,5,6,7-hexahydro-N,N-dipropylcyclopent[f]isoindol-6-amine (38) was treated with 2-(benzoylaminomethyl)thiophene-5-sulfonyl chloride. Crystallization from methanol gave 45 as tan crystals (m.p. 160–161, 186–187° C.).

EXAMPLE 28

2-[(2,3-Dichlorothiophene)-5-sulfonyl]-1,2,3,5,6,7-hexahydro-N,N-dipropylcyclopent[f]isoindol-6-amine. 46

Using procedure 9, 1,2,3,5,6,7-hexahydro-N,N-dipropylcyclopent[f]isoindol-6-amine (38) was treated with 2,3-dichlorothiophene-5-sulfonyl chloride. Crystallization from methanol gave 46 as tan crystals (m.p. 150–151° C.).
Procedure 30: t-Butyl [6,7-dihydro-3-[[benzyloxycarbonyl]aminomethyl]-5H-cyclopenta[c]pyridin-6-yl]carbamate. 55

A solution of benzyl chloroformate (17.1 g, 0.100 mol) in chloroform (50 ml) was added dropwise at room temperature over a period of 10 minutes to a mixture of aminoacetonitrile hydrochloride (13.89 g, 0.150 mol) and sodium carbonate (21.2 g, 0.200 mol) in water (50 ml) and chloroform (20 ml) in a flask equipped with a mechanical stirrer. The mixture was stirred for 2 hours, diluted with water, and extracted twice with diethylether. The combined extracts were washed with brine and dried ($MgSO_4$). The solvent was removed under vacuum to leave an oil. Crystallization from ethyl acetate/hexane gave N-benzyloxycarbonyl-2-aminoacetonitrile as colorless crystals (m.p. 61–62).

Using the procedure of Vollhardt (*J. Chem. Soc., Chem. Comm.*, 133–134 (1982)), a solution of N-benzyloxy-2-aminoacetonitrile (1.91 g, 10.0 mmol) in p-xylene (50 ml) was heated under argon at 145° C. A solution of 4-(t-butyloxycarbonylamino)heptan-1,6-diyne (4.15 g, 20.0 mmol), N-benzyloxy-2-aminoacetonitrile (3–81 g, 20.0 mmol), and cyclopentadienylcobalt dicarbonyl (0.50 ml, ~2.8 mmol) in p-xylene (45 ml) under argon was added via syringe pump to the heated xylene solution at the rate of 1.5 ml/hour. After the addition was complete, the solvent was removed under vacuum to leave a dark oil. Purification by flash chromatography on silica gel eluting with ethyl acetate/hexane gave a tan solid. Crystallization from ethyl acetate/hexane gave 55 as tan crystals (m.p. 113–115° C.).

Procedure 31: Phenylmethyl [[6-(dipropylamino)-6,7-dihydro-5H-cyclopenta[c]pyridin-3-yl]methyl]carbamate. 56

Trifluoroacetic acid (25 ml) was added to t-butyl [6,7-dihydro-3-[[benzyloxycarbonyl]aminomethyl]-5H-cyclopenta[c]pyridin-6-yl]carbamate (55, 4.45 g, 11.2 mmol) at room temperature, and the mixture was stirred for 20 minutes. Excess trifluoroacetic acid was removed under vacuum, and the residue was partitioned between 1:1 tetrahydrofuran/diethylether and 5% sodium hydroxide solution. The aqueous solution was extracted twice more with 1:1 tetrahydrofuran/diethylether, and the combined extracts were washed with brine and dried ($Na_2SO_4$). The solvent was removed under vacuum to leave phenylmethyl [[6-amino-6,7-dihydro-5H-cyclopenta[c]pyridin-3-yl]methyl]carbamate as an amber oil.

A mixture of phenylmethyl [[6-amino-6,7-dihydro-5H-cyclopenta[c]pyridin-3-yl]methyl]carbamate (2.96 g, 10.4 mmol), 1-bromopropane (5.2 g, 4.2 mmol), and potassium carbonate (3.60 g, 26.0 mmol) in acetonitrile (30 ml) was stirred at reflux for 17 hours. The mixture was diluted with water and extracted twice with diethylether. The combined extracts were washed with brine and dried ($MgSO_4$). The solvent was removed under vacuum to leave a dark oil. Purification by flash chromatography on silica gel eluting with tetrahydrofuran/ethyl acetate gave a dark oil. The compound was treated with activated charcoal in ethyl acetate and filtered through diatomaceous earth to give 56 as an amber oil.

Procedure 32
3-Aminomethyl-6-(dipropylamino)-6,7-dihydro-5H-cyclopenta[c]pyridine. 57

A mixture of phenylmethyl [[6-(dipropylamino)-6,7-dihydro-5H-cyclopenta[c]pyridin-3-yl]methyl]carbamate (56, 1.35 g, 3.54 mmol) and 10% palladium on carbon in absolute ethanol was hydrogenated for 3 hours at 50 psi hydrogen. The mixture was filtered through diatomaceous earth, and the filtrate was evaporated under vacuum to leave 57 as a yellow oil.

EXAMPLE 29

4-Chloro-N-[[6-(dipropylamino)-6,7-dihydro-5H-cyclopenta[c]pyridin-3-yl]methyl]benzenesulfonamide. 58

Using procedure 9, 3-(aminomethyl)-6-(dipropylamino)-6,7-dihydro-5H-cyclopenta[c]pyridine (57, 0.29 g, 1.2 mmol) was treated with 4-chlorobenzenesulfonyl chloride (0.25 g, 1.2 mmol). After extraction, etc., purification by flash chromatography on silica gel eluting with tetrahydrofuran/ethyl acetate gave an off-white solid. Crystallization from ethyl acetate/hexane gave 58 as off-white crystals (m.p. 125–126.5° C.).

EXAMPLE 30

2-Cyano-N-[[6-(dipropylamino)-6,7-dihydro-5H-cyclopenta[c]pyridin-3-yl]methyl]benzenesulfonamide. 59

Using procedure 9, 3-(aminomethyl)-6-(dipropylamino)-6,7-dihydro-5H-cyclopenta[c]pyridine (57, 0.42 g, 1.7 mmol) was treated with 2-cyanobenzenesulfonyl chloride (0.35 g, 1.7 mmol). Purification by flash chromatography on silica gel eluting with tetrahydrofuran in ethyl acetate gave an oil. Crystallization from ethyl acetate/hexane gave 59 as off-white crystals (m.p. 112–113° C.).

EXAMPLE 31

4-Chloro-N-[[6-(dipropylamino)-6,7-dihydro-5H-cyclopenta[c]pyridin-3-yl]methyl]benzamide. 60

Using procedure 11, 3-(aminomethyl)-6-(dipropylamino)-6,7-dihydro-5H-cyclopenta[c]pyridine (57, 0.43 g, 1.7 mmol) was treated with 4-chlorobenzoyl chloride (0.32 g, 1.8 mmol). Purification by flash chromatography on silica gel eluting with tetrahydrofuran/ethyl acetate gave a tan solid. Crystallization from ethyl acetate/hexane gave 60 as gray crystals (m.p. 101.5–103° C.).

EXAMPLE 32

Procedure 33. N-(4-Chlorophenyl)-N'-[[6-(dipropylamino)-6,7-dihydro-5H-cyclopenta[c]pyridin-3-yl]methyl]urea. 61

3-(Aminomethyl)-6-(dipropylamino)-6,7-dihydro-5H-cyclopenta[c]pyridine (57, 0.42 g, 1.7 mmol) was added to a solution of 4-chlorophenyl isocyanate (0.28 g, 1.8 mmol) in toluene (5 ml). The mixture was stirred at room temperature for 18 hours, and the solvent was removed under vacuum to leave an oil. The compound was stirred for 10 minutes with 5% hydrochloric acid solution, basified with 10% sodium carbonate solution, and extracted twice with ethyl acetate. The combined extracts were washed with brine and dried ($MgSO_4$). The solvent was removed under vacuum to leave an oil. Purification by flash chromatography on silica gel eluting with tetrahydrofuran in ethyl acetate gave a light amber solid. Crystallization from ethyl acetate/hexane gave 61 as gray crystals (m.p. 120–121° C.).

EXAMPLE 33

N-(4-Cyanophenyl)-N'-[[6-(dipropylamino)-6,7-dihydro-5H-cyclopenta[c]pyridin-3-yl]methyl]urea. 62

Using procedure 33, 3-(aminomethyl)-6-(dipropylamino)-6,7-dihydro-5H-cyclopenta[c]pyridine (57, 0.495 g, 2.00 mmol) was treated with 4-cyanophenyl isocyanate (0.29 g, 2.0 mmol). Purification by flash chromatography on silica gel eluting with tetrahydrofuran/ethyl acetate gave a light amber oil. Crystallization from ethyl acetate/hexane gave 62 as tan crystals (m.p. 135.5–136.5° C.).

Procedure 34. 6-Propylamino-4,5,6,7-tetrahydrobenzothiazole. 64

Sodium cyanoborohydride (25 g) was added to 4,5,6,7-tetrahydrobenzothiazol-6-one (63) (*Helv. Chim. Acta* 1994 1256) (14.5 g), propylamine (40 ml), glacial acetic acid (54 ml), methanol (500 ml) and THF (200 ml) in an ice bath. After 3.5 hours at room temperature, solvent was removed under vacuum and the residue was partitioned between aqueous sodium carbonate and ether/THF. The ether layer was washed with water and then 2N hydrochloric acid. This acid layer was basified and then extracted with diethyl ether/THF. This ether layer was washed with water and brine and was dried with sodium sulfate. Solvent was removed under vacuum to give 4.8 g of 64 as a liquid.

Procedure 35: tert-Butyl (2-formyl-4,5,6,7-tetrahydro-N-propyl-6-benzothiazolamine)carbamate. 65

6-Propylamino-4,5,6,7-tetrahydrobenzothiazole (64) (4.8 g) and di-tert-butyl dicarbonate (5.8 g) were combined in THF at 45° C. After 4.5 hours, solvent was removed and the residue was chromatographed on silica gel, eluting with ethyl acetate/hexane to give 5.8 g of a liquid after removal of solvent. n-Butyllithium (1.6 M in hexane, 7.4 ml) was added to this carbamate (3.0 g) in dry THF (25 ml) at −78° C. After 20 minutes, dry N,N-dimethylformamide (2.4 ml) was added and the cold bath removed. After 90 minutes, the solution was partitioned between water and ether. The ether layer was washed with water and brine and dried over sodium sulfate. The solvent was removed under vacuum and the residue was chromatographed on silica gel (ethyl acetate/hexane) to give 4.5 g of 65 as a liquid.

Procedure 36: tert-Butyl (2-hydroxyimino)methyl-4,5,6,7-tetrahydro-N-propyl-6-benzothiazolamine)carbamate. 66

Hydroxylamine hydrochloride (1.1 g) was added to tert-butyl (2-formyl-4,5,6,7-tetrahydro-N-propyl-6-benzothiazolamine)carbamate (65) (4.3 g), sodium hydroxide (1.3 g) and water. After 5 minutes, carbon dioxide was bubbled through the solution. The mixture was partitioned between water and ether/THF. The ether layer was washed with water and brine and was dried with sodium sulfate. Solvent was removed and the residue was chromatographed on silica gel (dichloromethane/ethyl acetate/hexane) to give 3.9 g of 66 as a solid.

Procedure 37: tert-Butyl (2-aminomethyl-4,5,6,7-tetrahydro-N-propyl-6-benzothiazolamine)carbamate. 67

Devarda's alloy (alloy of 50% copper, 45% aluminum, 5% zinc) (75 g) was added to tert-Butyl (2-hydroxyimino) methyl-4,5,6,7-tetrahydro-N-propyl-6-benzothiazolamine) carbamate (66) (4.0 g), sodium hydroxide (2N aqueous, 200 ml) and methanol (50 ml) and heated at 42° C. for 30 minutes. The mixture was extracted with diethyl ether/THF and the ether layer was washed with water and brine, and then dried with sodium sulfate. Solvent was removed under vacuum to give 2.9 g of 67 as a liquid.

EXAMPLE 34

N-(4-Chlorophenyl)-N'-[[4,5,6,7-tetrahydro-6-(propylamino)-2-benzothiazolyl]methyl]urea. 68

Using procedure 19, tert-butyl (R)-(2-aminomethyl-4,5, 6,7-tetrahydro-N-propyl-6-benzothiazolamine)carbamate (67) (0.90 g) was treated with 4-chlorophenyl isocyanate (0.46 g); then with trifluoroacetic acid to give 0.32 g of 68 as a solid, m.p. 125–130° C.

Procedure 38: 2-(Dipropylamino)-2,3-dihydro-6-(phenylmethoxy)-1H-inden-5-yl trifluoromethanesulfonate 70

Sodium hydride (0.96 g, 24 mmol) was washed with hexane under nitrogen and suspended in DMF (10 mL). 2-(Dipropylamino)-2,3-dihydro-6-hydroxy-1H-inden-5-yl trifluoromethanesulfonate (69, 7.6 g, 20 mmol) in DMF (30 mL) was added dropwise at 0–5° C. over 30 min and the mixture stirred 30 min. Benzyl bromide (5.13 g, 30 mmol) in DMF (5 mL) was added and the resulting mixture was stirred 1 h. The reaction was quenched with saturated NaHCO₃ and extracted with EtOAc. The organic layer was washed with water, brine, dried (MgSO₄), filtered and concentrated to give the crude product. Chromatographic purification yielded pure product 70 as an oil that was converted into the HCl salt and crystallized from EtOAc/MeOH/hexane to give a white solid (mp 162–163° C.).

6-Butoxy-2-(dipropylamino)-2,3-dihydro-1H-inden-5-yl trifluoromethanesulfonate 71

Using procedure 38, 2-(dipropylamino)-2,3-dihydro-6-hydroxy-1H-inden-5-yl trifluoromethanesulfonate (69, 0.38 g, 1 mmol) was treated with bromobutane (0.27 g, 2 mmol). Chromatographic purification yielded pure product 71 as a oil which was converted into the HCl salt and crystallized from EtOAc/hexane to give a white solid (mp 148–149° C.).

2-(Dipropylamino)-2,3-dihydro-6-propoxy-1H-inden-5-yl trifluoromethanesulfonate 72

Using procedure 38, 2-(dipropylamino)-2,3-dihydro-6-hydroxy-1H-inden-5-yl trifluoromethanesulfonate (69, 1.9 g, 5 mmol) was treated with propylbromide (2.5 g, 20 mmol). Chromatographic purification yielded pure product 72 as a oil which was converted into the HCl salt and crystallized from EtOAc/hexane to give a white solid (mp 169–170° C.)

2-(Dipropylamino)-6-ethoxy-2,3-dihydro-1H-inden-5-yl trifluoromethanesulfonate 73

Using procedure 38, 2-(dipropylamino)-2,3-dihydro-6-hydroxy-1H-inden-5-yl trifluoromethanesulfonate (69, 1.9 g, 5 mmol) was treated with bromoethane (2.2 g, 20 mmol). Chromatographic purification yielded pure product 73 as a oil which was converted into the HCl salt and crystallized from EtOAc/hexane to give a white solid (mp 181–182 ° C.)

Procedure 39: Methyl 2-(dipropylamino)-2,3-dihydro-6-(phenylmethoxy)-1H-indene-5-carboxylate 74

A mixture of 2-(Dipropylamino)-2,3-dihydro-6-(phenylmethoxy)-1H-indene-5-yl trifluoromethanesulfonate (70, 2.6 g, 5.6 mmol), palladium acetate (0.13 g, 0.56 mmol), 1,3-bis(diphenylphosphino-propane) (0.3 g, 0.73 mmol), triethylamine (0.7 mL, 6.3 mmol), methanol (6 mL), and DMF (18 mL) was heated at 60–70° C. with CO gas introduction. After 24 h, the reaction is quenched with saturated NaHCO₃, extracted with EtOAc, washed with water, brine, dried (MgSO₄), filtered and concentrated. Chromatographic purification yielded product 74 that was converted to the HCl salt and crystallized from EtOAc/MeOH to give a white solid (m.p. 181–182° C.).

Methyl 6-butoxy-2-(dipropylamino)-2,3-dihydro-1H-indene-5-carboxylate 75

Using procedure 39, 6-Butoxy-2-(dipropylamino)-2,3-dihydro-1H-inden-5-yl trifluoromethanesulfonate (71, 2.2 g, 5 mmol) was converted to methyl 6-butoxy-2-(dipropylamino)-2,3-dihydro-1H-indene-5-carboxylate 75 and crystallized from EtOAc/hexane as the HCl salt (m.p. 140–141° C.).

Methyl 2-(dipropylamino)-2,3-dihydro-6-propoxy-1H-indene-5-carboxylate 76

Using procedure 39, 2-(Dipropylamino)-2,3-dihydro-6-propoxy-1H-inden-5-yl trifluoromethanesulfonate (72, 2.96 g, 7 mmol) was converted to methyl 2-(dipropylamino)-2,3-dihydro-6-propoxy-1H-indene-5-carboxylate 76 and crystallized from EtOAc/hexane as the HCl salt (m.p. 175–176° C.).

Methyl 2-(dipropylamino)-6-ethoxy-2,3-dihydro-1H-indene-5-carboxylate 77

Using procedure 39, 2-(Dipropylamino)-6-ethoxy-2,3-dihydro-1H-inden-5-yl trifluoromethanesulfonate (73, 2.3 g, 5.7 mmol) was converted to methyl 2-(dipropylamino)-6-ethoxy-2,3-dihydro-1H-indene-5-carboxylate 77 and crystallized from EtOAc/hexane as the HCl salt (m.p. 168–169° C.).

EXAMPLE 35

Procedure 40: 2-(Dipropylamino)-2,3-dihydro-6-(phenylmethoxy)-1H-indene-5-carboxamide 78

To a solution of methyl 2-(dipropylamino)-2,3-dihydro-6-(phenylmethoxy)-1H-indene-5-carboxylate (74, 0.95 g, 2.5 mmol) and formamide (1.1 g, 25 mmol) in DMF (10 mL) at 100° C. was added 25% sodium methoxide in methanol (2.5 mmol, 0.57 mL) dropwise. The mixture stirred for 2 h. The reaction was cooled to rt and quenched with water (100 mL). The resulting precipitate was stirred for 0.5 h and the solvent was removed via filtration. This solid was crystallized from EtOAc/MeOH to give a white solid that was converted into the HCl salt and crystallized from EtOAc/MeOH to give the title compound 78 as a white solid (m.p. 247–248° C.).

EXAMPLE 36

6-Butoxy-2-(dipropylamino)-2,3-dihydro-1H-indene-5-carboxamide 79

Using procedure 40, methyl 6-butoxy-2-(dipropylamino)-2,3-dihydro-1H-indene-5-carboxylate (75, 1 g, 2.9 mmol) was converted to 79 and crystallized from EtOAc/MeOH as the HCl salt (m.p. 215–216° C.).

EXAMPLE 37

2-(Dipropylamino)-2,3-dihydro-6-propoxy-1H-indene-5-carboxamide 80

Using procedure 40, methyl 2-(dipropylamino)-2,3-dihydro-6-propoxy-1H-indene-5-carboxylate (76, 1.1 g, 3.5 mmol) was converted to 80 and crystallized from EtOAc/EtOH as the HCl salt (m.p. 238–239° C.).

EXAMPLE 38

2-(Dipropylamino)-6-ethoxy-2,3-dihydro-1H-indene-5-carboxamide 81

Using procedure 40, methyl 2-(dipropylamino)-6-ethoxy-2,3-dihydro-1H-indene-5-carboxylate (77, 1.1 g, 3.5 mmol) was converted to 81 and crystallized from EtOAc/MeOH as the HCl salt (m.p. 236–237° C.).

EXAMPLE 39

Procedure 41: 6-Butoxy-2-(dipropylamino)-2,3-dihydro-N-methyl-1H-indene-5-carboxamide 82

To a mixture of methyl 6-butoxy-2-(dipropylamino)-2,3-dihydro-1H-indene-5-carboxylate (75, 0.35 g, 1 mmol) and N-methylformamide (0.59 g, 10 mmol) in DMF (10 mL) at 100° C. and 25% was added sodium methoxide in methanol (0.22 mL, 1 mmol) dropwise over a period of 10 min. The resulting mixture is cooled to room temperature and quenched with water (100 mL). The resulting solid was purified by chromatography to give an oil that was converted into the HCl salt and crystallized from EtOAc/MeOH to yield the title compound 82 as a white solid (m.p.129–130° C.).

EXAMPLE 40

6-Ethoxy-2-(dipropylamino)-2,3-dihydro-N-methyl-1H-indene-5-carboxamide 83

Using procedure 41, methyl 2-(dipropylamino)-6-ethoxy-2,3-dihydro-1H-indene-5-carboxylate (77, 0.32 g, 1 mmol) was treated with N-methylformamide (0.58 mL, 10 mmol). Chromatographic purification yielded pure product 83 as a oil which was converted into the HCl salt and crystallized from EtOAc/MeOH to give a white solid (m.p. 156–159° C.).

EXAMPLE 41

2-(Dipropylamino)-6-ethoxy-2,3-dihydro-N-(phenylmethyl)-1H-indene-5- carboxamide 84

Using procedure 41, methyl 2-(dipropylamino)-6-ethoxy-2,3-dihydro-1H-indene-5-carboxylate (77, 0.32 g, 1 mmol) was treated with N-benzylformamide (1.35 g, 10 mmol). Chromatographic purification yielded pure product 84 as a oil which was converted into the HCl salt and crystallized from EtOAc to give a white solid (m.p. 219–221° C.).

EXAMPLE 42

Procedure 42: 2-(Dipropylamino)-6-ethoxy-N-(2-fluoroethyl)-2,3-dihydro-1H-indene-5-carboxamide 85

Sodium hydride (0.05 g, 1.2 mmol) was washed with hexane under nitrogen and suspended in DMF (5 mL). 2-(Dipropylamino)-6-ethoxy-2,3-dihydro-1H-indene-5-carboxamide (81, 0.15 g, 0.5 mmol) in DMF (5 mL) was added dropwise at 0–5° C. over 30 min and the mixture stirred 30 min. 1-Bromo-2-fluoroethane (0.26 g, 2 mmol) in DMF (5 mL) was added and the resulting mixture was stirred 3 h. The reaction was quenched with saturated NaHCO$_3$ and extracted with EtOAc. The organic layer is washed with water, brine, dried (MgSO$_4$), filtered and concentrated to give crude product. Chromatographic purification yielded pure product 85 as an oil that was converted into the HCl salt and crystallized from EtOAc/hexane/MeOH to give a white solid (m.p. 158–159° C.).

Procedure 43: 2-(Dipropylamino)-2,3-dihydro-6-hydroxy-1H-indene-5-carboxamide 87

To a solution of methyl 2-(dipropylamino)-2,3-dihydro-6-hydroxy-1H-indene-5-caboxylate (86, 0.93 g, 2.9 mmol) and formamide (1.2 mL, 29 mmol) in DMF (20 mL) at 100° C. was added 25% sodium methoxide in methanol (1.3 mL, 5.8 mmol) dropwise. The mixture stirred for 4 h. The reaction was quenched with saturated NaHCO$_3$ and extracted with EtOAc. The organic layer is washed with water, brine dried (MgSO$_4$), filtered and concentrated to give the crude product. Chromatographic purification yielded pure product as an oil that was converted into the HCl salt and crystallized from EtOAc/MeOH to give the title compound 87 as a white solid (m.p. 266–267° C.).

EXAMPLE 43

Procedure 44: 2-(Dipropylamino)-6-(2-fluoroethoxy)-2,3-dihydro-1H-indene-5-carboxamide 88

A mixture of 2-(Dipropylamino)-2,3-dihydro-6-hydroxy-1H-indene-5-carboxamide (87, 0.14 g, 0.5 mmol), potassium carbonate (0.2 g, 1.5 mmol), 1-bromo-2-fluoroethane (0.19 g, 1.5 mmol) in DMF (10 mL) was stirred at room temperature for 5 h. The mixture was quenched with water, and extracted with EtOAc. The organic layer was washed with brine, dried (MgSO$_4$), filtered and concentrated. Chromatographic purification yielded a pale yellow solid which was converted into the HCl salt and crystallized from EtOAc/MeOH to give the title compound 88 as an off-white solid (m.p. 232–233° C.).

EXAMPLE 44

2-(Dipropylamino)-6-(3-fluoropropoxy)-2,3-dihydro-1H-indene-5-carboxamide 89

Using procedure 44, 2-(Dipropylamino)-2,3-dihydro-6-hydroxy-1H-indene-5-carboxamide (87, 0.19 g, 0.7 mmol) was treated with 1-bromo-3-fluoropropane (0.296 g, 2.1 mmol). Chromatographic purification yielded pure product 89 as a oil which was converted into the HCl salt and crystallized from EtOAc/MeOH to give a white solid (m.p. 219–220° C.).

EXAMPLE 45

2-(Dipropylamino)-6-ethoxy-N-ethyl-2,3-dihydro-1H-indene-5-carboxamide 90

Using procedure 44, 2-(Dipropylamino)-2,3-dihydro-6-hydroxy-1H-indene-5-carboxamide (87, 0.36 g, 1.15 mmol) was treated with bromoethane (0.38 g, 3.45 mmol). Chromatographic purification yielded pure product as a oil 90 which was converted into the HCl salt and crystallized from EtOAc/MeOH to give a white solid (m.p. 145–146° C.).

Procedure 45: 2-(dipropylamino)-2,3-dihydro-1H-indene-5,6-dicarboxylate 92

The dimethyl 2-(dipropylamino)-2,3-dihydro-1H-indene-5,6-dicarboxylate (91, 10.0 g, 30.0 mmol) was refluxed at 70° C. with NaOH (2.4 g, 60.0 mmol) in 1:3 $H_2O$/MeOH (100 mL) for 3 h. The reaction was concentrated and lyophilized. The resulting solid was heated in THF/MeOH (1:1) and allowed to cool overnight. The resulting solid 92 was obtained via filtration and dried (m.p. >300° C.).

EXAMPLE 46

Procedure 46: 6-(Dipropylamino)-6,7-dihydrocyclopent[f]isoindole-1,3(2H,5H)-dione 93

A solution of 2-(dipropylamino)-2,3-dihydro-1H-indene-5,6-dicarboxylate (92, 3.00 g, 8.6 mmol), ($NH_4$)OAc (6.63 g, 86.0 mmol), and conc. HCl (1.7 mL) in glacial HOAc (200 mL) was refluxed at 119° C. for 20 h. The reaction was cooled, concentrated, and azeotroped with toluene to give a white solid. The residue was diluted with $H_2O$, basified with sat'd $NaHCO_3$ to pH >9, and filtered through a sintered glass funnel. The collected solid was diluted with MeOH and azeotroped numerous times with toluene until dry. The solid was dissolved in hot MeOH, filtered through filter paper and recrystallized from additional hot MeOH to give 93 as a tan solid. The solid was converted to the HCl salt and recrystallized from hot MeOH/EtOAc to give a white solid (m.p. 290–291° C.).

EXAMPLE 47

Procedure 47. 6-(Dipropylamino)-3,5,6,7-tetrahydrocyclopent[f]isoindol-1(2H)-one 94

(Ref. Brewster, J. H.; Fusco A. M. *J.Org. Chem.*, 28, 501–503 (1963)) A solution of 6-(dipropylamino)-6,7-dihydrocyclopent[f]isoindole-1,3(2H,5H)-dione 93 (0.45 g, 1.6 mmol) in glacial HOAc (50 mL) was treated with Zinc dust (1.05 g, 16.0 mmol) then refluxed at 113° C. for 24 h. The reaction was cooled to r.t., diluted with MeOH and filtered through a pad of celite. The filtrate was concentrated and the residue was diluted with $H_2O$, basified with sat'd $Na_2CO_3$, and extracted with $CH_2Cl_2$. The organic layers were washed with brine, dried ($MgSO_4$), and concentrated. The resulting solid was purified using silica gel, eluting with 2:1 heptane/acetone to give 94 as a white solid (m.p. 206–208° C.).

EXAMPLE 48

Procedure 48. 6-(Dipropylamino)-2-ethyl-6,7-dihydrocyclopent[f]isoindole-1,3(2H,5H)-dione 95

To a solution of 6-(dipropylamino)-6,7-dihydrocyclopent[f]isoindole-1,3(2H,5H)-dione (93, 0.15 g, 0.52 mmol) in DMF (10 mL) at 0° C. was added anhydrous $K_2CO_3$ (0.14 g, 1.04 mmol) followed by ethyl bromide (0.06 mL, 0.79 mmol). The reaction was stirred at 0° C. for 2 hr then allowed to warm to r.t. Continued stirring overnight then quenched with $H_2O$. The solution was extracted with $CH_2Cl_2$ and the organic layers were washed with brine, dried ($MgSO_4$), and concentrated. The residue was further concentrated on the high vac to remove any excess DMF and the resulting greenish solid was purified using silica gel, eluting with 3:1 hexane/acetone to give 95 as an off-white solid. The solid was converted to an HCl salt and recrystallized from hot MeOH/EtOAc to give 95 as a white solid (m.p. 225–230° C.).

EXAMPLE 49

6-(Dipropylamino)-6,7-dihydro-2-propylcyclopent[f]isoindole-1,3(2H,5H)-dione 96

Using procedure 48, 6-(dipropylamino)-6,7-dihydrocyclopent[f]isoindole-1,3(2H,5H)-dione (93, 0.15 g, 0.52 mmol) was treated with 1-bromopropane (0.07 mL, 0.78 mmol). Purification via silica gel, eluting with 3:1 hexane/acetone, afforded a solid that was converted to an HCl salt and recrystallized from hot MeOH/EtOAc to give 96 as a white solid (m.p. 217–218° C.).

EXAMPLE 50

4-[[6-(Dipropylamino)-3,5,6,7-tetrahydro-1,3-dioxocyclopent[f]isoindol-2(1H)-yl]methyl]benzonitrile 97

Using procedure 48, 6-(dipropylamino)-6,7-dihydrocyclopent[f]isoindole-1,3(2H,5H)-dione (93, 0.12 g, 0.4 mmol) was treated with alpha-bromo-p-tolunitrile (0.08 mL, 0.4 mmol). Purification using silica gel, eluting with 3:1 hexane/acetone, afforded a solid that was converted to an HCl salt and recrystallized from hot MeOH/EtOAc to give 97 as a white solid (m.p. 263–264° C.).

EXAMPLE 51

2-(1H-Benzotriazol-1-ylmethyl)-6-(dipropylamino)-6,7-dihydrocyclopent[f]isoindole-1,3-(2H,5H)-dione 98

Using procedure 48, 6-(dipropylamino)-6,7-dihydrocyclopent[f]isoindole-1,3(2H,5H)-dione (93, 0.14 g, 0.5 mmol) was treated with 1-(chloromethyl)-1H-benzotriazole (0.08 g, 0.5 mmol). Purification using silica gel, eluting with 3:1 hexane/acetone, afforded a solid that was converted to an HCl salt and recrystallized from hot MeOH/EtOAc to give 98 as a white solid (m.p. 254–256° C.).

EXAMPLE 52

6-(Dipropylamino)-6,7-dihydro-2-[(2-methyl-5-thiazolyl)methyl]cyclopent[f]isoindole-1,3(2H,5H)-dione 99

Using procedure 48, 6-(dipropylamino)-6,7-dihydrocyclopent[f]isoindole-1,3(2H,5H)-dione (93, 0.14 g, 0.5 mmol) was treated with 4-chloromethyl-2-methylthiazole hydrochloride (0.18 g, 1.0 mmol). Purification using silica gel, eluting with 4:1 hexane/acetone+0.1% MeOH, afforded a solid that was converted to an HCl salt and recrystallized from hot MeOH/EtOAc to give 99 as a white solid (m.p. 235–236° C.).

EXAMPLE 53
6-(Dipropylamino)-6,7-dihydro-2-(1,2,4-oxadiazol-3-ylmethyl)cyclopent[f]isoindole-1,3(2H,5H)-dione 100

Using procedure 48, 6-(dipropylamino)-6,7-dihydrocyclopent[f]isoindole-1,3(2H,5H)-dione (93, 0.14 g, 0.5 mmol) was treated with 3-(chloromethyl)-1,2,4-oxadiazole (0.09 g, 0.75 mmol). Purification using silica gel, eluting with 7:1 $CH_2Cl_2$/acetone, afforded a solid that was converted to an HCl salt and recrystallized from $CH_2Cl_2$/$Et_2O$ to give 100 as a white solid (m.p. 190–191° C.).

EXAMPLE 54
Procedure 49. 6-(Dipropylamino)-2-[(4-fluorophenyl)methyl]-6,7-dihydrocyclopent[f]isoindole-1,3(2H,5H)-dione 101

(O'Reilly, N. J., Derwin, W. S., Fertel, L. B., Lin, H. C., Synlett., (1990) 609–610.) A solution of 2-(dipropylamino)-2,3-dihydro-1H-indene-5,6-dicarboxylate (92, 0.35 g, 1.0 mmol) and 4-fluorobenzylamine (0.15 mL, 1.3 mmol) in glacial HOAc (30 mL) was refluxed at 113° C. After 4 h, the reaction was cooled to r.t., concentrated, then azeotroped with toluene. The residue was diluted with water and basified with sat'd $Na_2CO_3$ (or sat'd $NaHCO_3$) to pH>12. The solution was extracted with $CH_2Cl_2$ and the organic layers were washed with brine, dried ($MgSO_4$), and concentrated. The residue was purified by using silica gel, eluting with 4:1 $CH_2Cl2$/acetone+0.1 % MeOH, to give 101 as a light yellow oil that was converted to an HCl salt and recrystallized from MeOH/EtOAc to give a white solid (m.p. 251–253° C.).

EXAMPLE 55
2-[(4-Chlorophenyl)methyl]-6-(dipropylamino)-6,7-dihydrocyclopent[f]isoindole-1,3(2H,5H)-dione 102

Using procedure 49, 2-(dipropylamino)-2,3-dihydro-1H-indene-5,6-dicarboxylate (92, 0.35 g, 1.0 mmol) was treated with 4-chlorobenzylamine (0.17 mL, 1.4 mmol). Purification using silica gel, eluting with 5:1 hexane/acetone, afforded an oil that was converted to an HCl salt and recrystallized from hot MeOH/EtOAc to give 102 as a white solid (m.p. 260–261° C.).

EXAMPLE 56
6-(Dipropylamino)-6,7-dihydro-2-[(2-methoxyphenyl)methyl]cyclopent[f]isoindole-1,3(2H,5H)-dione 103

Using procedure 49, 2-(dipropylamino)-2,3-dihydro-1H-indene-5,6-dicarboxylate (92, 0.35 g, 1.0 mmol) was treated with o-methoxybenzylamine (0.18 mL, 1.4 mmol). Purification using silica gel, eluting with 5:1 $CH_2Cl_2$/acetone, afforded an oil that was converted to an HCl salt and recrystallized from hot MeOH/EtOAc to give 103 as a white solid (m.p.205° C.).

EXAMPLE 57
6-(Dipropylamino)-6,7-dihydro-2-[(3-methoxyphenyl)methyl]cyclopent[f]isoindole-1,3(2H,5H)-dione 104

Using procedure 49, 2-(dipropylamino)-2,3-dihydro-1H-indene-5,6-dicarboxylate (92, 0.35 g, 1.0 mmol) was treated with m-methoxybenzylamine (0.17 mL, 1.3 mmol). Purification using silica gel, eluting with 3:1 hexane/acetone, afforded an oil that was converted to an HCl salt and recrystallized from hot MeOH/EtOAc to give 104 as a white solid (m.p. 247–248° C.).

EXAMPLE 58
6-(Dipropylamino)-6,7-dihydro-2-[(4-methoxyphenyl)methyl]cyclopent[f]isoindole-1,3(2H,5H)-dione 105

Using procedure 49, 2-(dipropylamino)-2,3-dihydro-1H-indene-5,6-dicarboxylate (92, 0.10 g, 0.28 mmol) was treated with p-methoxybenzylamine (0.05 mL, 0.4 mmol). Purification using silica gel, eluting with 5:1 $CH_2Cl_2$/acetone, afforded an oil that was converted to an HCl salt and recrystallized from EtOAc to give 105 as a white solid (m.p. 255–256° C.).

EXAMPLE 59
2-[(3,4-Dimethoxyphenyl)methyl]-6-(dipropylamino)-6,7-dihydrocyclopent[f]isoindole-1,3(2H,5H)-dione 106

Using procedure 49, 2-(dipropylamino)-2,3-dihydro-1H-indene-5,6-dicarboxylate (92, 0.35 g, 1.0 mmol) was treated with veratrylamine (0.20 mL, 1.3 mmol). Purification using silica gel, eluting with 3:1 hexane/acetone, afforded an oil that was converted to an HCl salt and recrystallized from hot MeOH/EtOAc to give 106 as a white solid (m.p. 233–235° C.).

EXAMPLE 60
6-(Dipropylamino)-6,7-dihydro-2-[[4-(trifluoromethoxy)phenyl]methyl]cyclopent[f]isoindole-1,3(2H,5H)-dione 107

Using procedure 49, 2-(dipropylamino)-2,3-dihydro-1H-indene-5,6-dicarboxylate (92, 0.35 g, 1.0 mmol) was treated with 4-trifluoromethyl-benzylamine (0.25 mL, 1.3 mmol). Purification using silica gel, eluting with 3:1 $CH_2Cl_1$/acetone, afforded an oil that was converted to an HCl salt and recrystallized from hot MeOH/EtOAc to give 107 as a white solid (m.p. 233–235° C.).

EXAMPLE 61
6-(Dipropylamino)-6,7-dihydro-2-(2-phenylethyl)cyclopent[f]isoindole-1,3(2H,5H)-dione 108

Using procedure 49, 2-(dipropylamino)-2,3-dihydro-1H-indene-5,6-dicarboxylate (92, 0.35 g, 1.0 mmol) was treated with 4-trifluoromethyl-benzylamine (0.2 mL, 1.4 mmol). Purification using silica gel, eluting with 4:1 $CH_2Cl_2$/acetone, afforded an oil that was converted to an HCl salt and recrystallized from hot MeOH/EtOAc to give 108 as a white solid (m.p. 229–230° C.).

EXAMPLE 62
4-[[6-(Dipropylamino)-3,5,6,7-tetrahydro-1,3-dioxocyclopent[f]isoindol-2(1H)-yl]methyl]benzenesulfonamide 109

Using procedure 49, 2-(dipropylamino)-2,3-dihydro-1H-indene-5,6-dicarboxylate (92, 0.35 g, 1.0 mmol) was treated with p-aminomethylbenzenesulfonamide (0.31 g, 1.4 mmol). Purification using silica gel, eluting with 4:1 $CH_2Cl_2$/acetone, afforded a solid that recrystallized from $CH_2Cl_2$/$Et_2O$/hexane to give 109 as a white solid (m.p. 190–194° C.).

EXAMPLE 63
Methyl 4-[[6-(dipropylamino)-3,5,6,7-tetrahydro-1,3-dioxocyclopent[f]isoindol-2(1H)-yl]methyl]benzoate 110

The 4-(aminomethyl)benzoic acid methyl ester was obtained from the conversion of 4-(aminomethyl)benzoic acid via esterification using MeOH/$H_2SO_4$. The ester was converted to the HCl salt and recrystallized from EtOAc (m.p. 238–240° C.).

Using procedure 49, 2-(dipropylamino)-2,3-dihydro-1H-indene-5,6-dicarboxylate (92, 0.35 g, 1.0 mmol) was treated with 4-(aminomethyl)benzoic acid methyl ester (0.28 g, 1.4 mmol). Purification using silica gel, eluting with 4:1 $CH_2Cl_2$/acetone, afforded an oil that was converted to an HCl salt and recrystallized from hot MeOH/EtOAc to give 110 as a white solid (m.p. 244–246° C.).

EXAMPLE 64
4-[[6-(Dipropylamino)-3,5,6,7-tetrahydro-1,3-dioxocyclopent[f]isoindol-2(1H)-yl]methyl]benzamide 111

The 4-(aminomethyl)benzamide was obtained from the conversion of 4-(aminomethyl)benzoic acid methyl ester via reaction with $NH_4OH$ using the procedure of Cliffton, J. E., et al., *J. Med. Chem.*, 1982, 25, 670–679. The amide was converted to the HCl salt and recrystallized from MeOH/EtOAc (m.p. 244–249° C.).

Using procedure 49, 2-(dipropylamino)-2,3-dihydro-1H-indene-5,6-dicarboxylate (92, 0.35 g, 1.0 mmol) was treated with 4-(aminomethyl)benzamide (0.26 g, 1.4 mmol). Purification using silica gel, eluting with 19:1 $CH_2Cl_2$/MeOH, afforded an oil that was converted to an HCl salt and recrystallized from hot MeOH to give 111 as a white solid (m.p. 294° C.).

EXAMPLE 65
6-(Dipropylamino)-6,7-dihydro-2-(2-phenylethyl)cyclopent[f]isoindole-1,3(2H,5H)-dione 112

Using procedure 49, 2-(dipropylamino)-2,3-dihydro-1H-indene-5,6-dicarboxylate (92, 0.35 g, 1.0 mmol) was treated with phenethylamine (0.16 mL, 1.3 mmol). Purification using silica gel, eluting with 3:1 $CH_2Cl_2$/acetone, afforded an oil that was converted to an HCl salt and recrystallized from hot MeOH/EtOAc to give 112 as a white solid (m.p. 235–240° C.).

EXAMPLE 66
6-(Dipropylamino)-6,7-dihydro-2-[2-(4-methoxyphenyl)ethyl]cyclopent[f]isoindole-1,3(2H,5H)-dione 113

Using procedure 49, 2-(dipropylamino)-2,3-dihydro-1H-indene-5,6-dicarboxylate (92, 0.35 g, 1.0 mmol) was treated with 4-methoxyphenethylamine (0.19 mL, 1.3 mmol). Purification using silica gel, eluting with 3:1 hexane/acetone, afforded an oil that was converted to an HCl salt and recrystallized from hot MeOH/EtOAc to give 113 as a white solid (m.p. 211–215° C.).

EXAMPLE 67
6-(Dipropylamino)-6,7-dihydro-2-(3-phenylpropyl)cyclopent[f]isoindole-1,3(2H,5H)-dione 114

Using procedure 49, 2-(dipropylamino)-2,3-dihydro-1H-indene-5,6-dicarboxylate (92, 0.35 g, 1.0 mmol) was treated with 3-phenylpropylamine(0.19 mL, 1.4 mmol). Purification using silica gel, eluting with 9:1 $CH_2Cl_2$/acetone, afforded an oil that was converted to an HCl salt and recrystallized from hot MeOH/EtOAc to give 114 as a white solid (m.p. 222–223° C.).

EXAMPLE 68
6-(Dipropylamino)-6,7-dihydro-2-(2-pyridinylmethyl)cyclopent[f]isoindole-1,3(2H,5H)-dione 115

Using procedure 49, 2-(dipropylamino)-2,3-dihydro-1H-indene-5,6-dicarboxylate (92, 0.35 g, 1.0 mmol) was treated with 2-aminomethylpyridine (0.4 mL, 4.0 mmol). Purification via using silica gel, eluting with 2:1 $CH_2Cl_2$/acetone, afforded an oil that was converted to an HCl salt and recrystallized from hot MeOH/EtOAc to give 115 as a white solid (m.p. 130–135° C.).

EXAMPLE 69
6-(Dipropylamino)-6,7-dihydro-2-(3-pyridinylmethyl)cyclopent[f]isoindole-1,3(2H,5H)-dione 116

Using procedure 49, 2-(dipropylamino)-2,3-dihydro-1H-indene-5,6-dicarboxylate (92, 0.35 g, 1.0 mmol) was treated with 3-aminomethylpyridine (0.14 mL, 1.4 mmol). Purification using silica gel, eluting with 19:1 $CH_2Cl_2$/MeOH sat'd with $NH_3$, afforded an oil that was converted to an HCl salt and recrystallized from hot MeOH/EtOAc to give 116 as a white solid (m.p. 141–146° C.).

EXAMPLE 70
6-(Dipropylamino)-6,7-dihydro-2-(4-pyridinylmethyl)cyclopent[f]isoindole-1,3(2H,5H)-dione 117

Using procedure 49, 2-(dipropylamino)-2,3-dihydro-1H-indene-5,6-dicarboxylate (92, 0.35 g, 1.0 mmol) was treated with 4-aminomethylpyridine (0.14 mL, 1.4 mmol). Purification using silica gel, eluting with 3:1 $CH_2Cl_2$/acetone, afforded an oil that was converted to an HCl salt and recrystallized from hot MeOH/EtOAc to give 117 as a white solid (m.p. 283–284° C.).

EXAMPLE 71
6-(Dipropylamino)-6,7-dihydro-2-[2-(1H-imidazol-4-yl)ethyl]cyclopent[f]isoindole-1,3(2H,5H)-dione 118

Using procedure 49, 2-(dipropylamino)-2,3-dihydro-1H-indene-5,6-dicarboxylate (92, 0.35 g, 1.0 mmol) was treated with histamine (0.16 g, 1.4 mmol). Purification using silica gel, eluting with 9:1 $CH_2Cl_2$/MeOH, afforded a solid that was converted to an HCl salt and recrystallized from hot MeOH/EtOAc to give 118 as a white solid (m.p. 190–191° C.).

EXAMPLE 72
6-(Dipropylamino)-6,7-dihydro-2-(2-thienylmethyl)cyclopent[f]isoindole-1,3(2H,5H)-dione 119

Using procedure 49, 2-(dipropylamino)-2,3-dihydro-1H-indene-5,6-dicarboxylate (92, 0.35 g, 1.0 mmol) was treated with 2-thiophene-methylamine (0.13 mL, 1.3 mmol). Purification using silica gel, eluting with 3:1 $CH_2Cl2$/acetone, afforded an oil that was converted to an HCl salt and recrystallized from hot MeOH/EtOAc to give 119 as a white solid (m.p. 220–225° C.).

EXAMPLE 73
6-(Dipropylamino)-6,7-dihydro-2-methylcyclopent[f]isoindole-1,3(2H,5H)- dione 120

Using procedure 49, 2-(dipropylamino)-2,3-dihydro-1H-indene-5,6-dicarboxylate (92, 0.3 g, 1.0 mmol) was treated with methylamine hydrochloride(1.35 g, 20.0 mmol). Purification on silica gel, eluting with 2:1 hexane/acetone, afforded an oil that was converted to an HCl salt and recrystallized from EtOAc/2-propanol to give 120 as a white solid (m.p. 245–246° C.).

EXAMPLE 74
6-(Dipropylamino)-6,7-dihydro-2-phenylcyclopent[f]isoindole-1,3(2H,5H)-dione 121

Using procedure 49, 2-(dipropylamino)-2,3-dihydro-1H-indene-5,6-dicarboxylate (92, 0.3 g, 1.0 mmol) was treated with aniline (0.11 g, 1.2 mmol). Purification on silica gel, eluting with 2:1 hexane/acetone, afforded a solid that was converted to an HCl salt and recrystallized from EtOAc/2-propanol to give 121 as a white solid (m.p. 241–242° C.).

EXAMPLE 75
4-[6-(Dipropylamino)-3,5,6,7-tetrahydro-1,3-dioxocyclopent[f]isoindol-2(1H)-yl]benzamide 122

Using procedure 49, 2-(dipropylamino)-2,3-dihydro-1H-indene-5,6-dicarboxylate (92, 0.3 g, 1.0 mmol) was treated with 4-aminobenzamide (1.4 g, 10.0 mmol). Purification on silica gel, eluting with 9:1 $CH_2Cl_2$/MeOH sat'd w/ $NH_3$, afforded a solid that was converted to an HCl salt and recrystallized from EtOAc/MeOH to give 122 as a white solid (m.p. 275–276° C.).

EXAMPLE 76

4-[6-(Dipropylamino)-3,5,6,7-tetrahydro-1,3-dioxocyclopent[f]isoindol-2(1H)-yl]benzonitrile 123

Using procedure 49, 2-(dipropylamino)-2,3-dihydro-1H-indene-5,6-dicarboxylate (92, 0.3 g, 1.0 mmol) was treated with 4-aminobenzonitrile (0.47 g, 4.0 mmol). Purification on silica gel, eluting with 3:1 hexane/acetone, afforded a solid that was converted to an HCl salt and recrystallized from EtOAc/ethanol to give 123 as a white solid (m.p. 250–251° C.).

EXAMPLE 77

6-(Dipropylamino)-6,7-dihydro-2-(phenylmethyl)cyclopent[f]isoindole-1,3(2H,5H)-dione 124

Using procedure 49, 2-(dipropylamino)-2,3-dihydro-1H-indene-5,6-dicarboxylate (92, 0.3 g, 1.0 mmol) was treated with benzylamine (0.44 mL, 4.0 mmol). Purification on silica gel, eluting with 3:1 hexane/acetone, afforded a solid that was converted to an HCl salt and recrystallized from EtOAc/2-propanol to give 124 as a white solid (m.p. 247–248° C.).

EXAMPLE 78

6-(Dipropylamino)-3,5,6,7-tetrahydro-2-(phenylmethyl)cyclopent[f]isoindol-1(2H)-one 125

Using procedure 47, 6-(Dipropylamino)-6,7-dihydro-2-(phenylmethyl)cyclopent[f]isoindole-1,3(2H,5H)-dione (124, 0.41 g, 1.0 mmol) was reduced with Zinc dust (0.65 g, 10.0 mmol) in glacial HOAc (20 mL). Purification on silica gel, eluting with 3:1 hexane/acetone gave an oil that was converted to an HCl salt and recrystallized from EtOAc/MeOH to give 125 as a white solid (m.p. 235–236° C.).

EXAMPLE 79

6-(Dipropylamino)-3,5,6,7-tetrahydro-2-methylcyclopent[f]isoindol-1(2H)-one 126

Using procedure 47, the 6-(dipropylamino)-6,7-dihydro-2-methylcyclopent[f]isoindole-1,3(2H,5H)-dione (120, 0.13 g, 0.4 mmol) was reduced with Zinc dust (0.26 g, 4.0 mmol) in glacial HOAc (10 mL). Purification via crystallization from EtOAc/MeOH gave an off-white solid that was converted to an HCl salt and recrystallized from EtOAc/MeOH to give 126 as a white solid (m.p. 242–243° C.).

EXAMPLE 80

6-(Dipropylamino)-3,5,6,7-tetrahydro-2-phenylcyclopent[f]isoindol-1(2H)-one 127

Using procedure 47, 6-(dipropylamino)-6,7-dihydro-2-phenylcyclopent[f]isoindole-1,3(2H,5H)-dione (121, 0.09 g, 0.23 mmol) was reduced with Zinc dust (0.15 g, 2.3 mmol) in glacial HOAc (5 mL). Purification on silica gel, eluting with 3:1 hexane/acetone gave an oil that was converted to an HCl salt and recrystallized from EtOAc/MeOH to give 127 as a white solid (m.p. 248–249° C.).

EXAMPLE 81

6-(Dipropylamino)-3,5,6,7-tetrahydro-2-[[4-(trifluoromethoxy)phenyl]methyl]cyclopent[f]isoindol-1(2H)-one 128

Using procedure 47, 6-(dipropylamino)-6,7-dihydro-2-[[4-(trifluoromethoxy)phenyl]methyl]cyclopent[f]isoindole-1,3(2H,5H)-dione (107, 0.17 g, 0.37 mmol) was reduced with Zinc dust (0.24 g, 3.7 mmol) in glacial HOAc (10 mL). The resulting solid was converted to an HCl salt and recrystallized from EtOAc/MeOH to give 128 as a white solid (m.p. 210–211° C.).

EXAMPLE 82

2-[(4-Chlorophenyl)methyl]-6-(dipropylamino)-3,5,6,7-tetrahydrocyclopent[f]isoindol-1(2H)-one 129

Using procedure 47, 2-[(4-Chlorophenyl)methyl]-6-(dipropylamino)-6,7-dihydrocyclopent[f]isoindole-1,3(2H,5H)-dione (102, 0.59 g, 1.43 mmol) was reduced with Zinc dust (0.94 g, 14.3 mmol) in glacial HOAc (100 mL). Purification using silica gel, eluting with 4:1 hexane/acetone, afforded an oil that was converted to an HCl salt and recrystallized from EtOAc/MeOH to give 129 as a white solid (m.p. 233–234° C.).

EXAMPLE 83

6-(Dipropylamino)-3,5,6,7-tetrahydro-2-[(4-methoxyphenyl)methyl]cyclopent[f]isoindol-1(2H)-one 130

Using procedure 47, 6-(dipropylamino)-6,7-dihydro-2-[(4-methoxyphenyl)methyl]cyclopent[f]isoindole-1,3(2H,5H)-dione (105, 0.27 g, 0.67 mmol) was reduced with Zinc dust (0.44 g, 6.7 mmol) in glacial HOAc (20 mL). Purification using silica gel, eluting with 8:1 $CH_2Cl_2$/acetone, afforded an oil that was converted to an HCl salt and recrystallized from EtOAc/MeOH to give 130 as a white solid (m.p. 227–228° C.).

EXAMPLE 84

6-(Dipropylamino)-3,5,6,7-tetrahydro-2-[[4-(trifluoromethyl)phenyl]methyl]cyclopent[f]isoindol-1(2H)-one 131

Using procedure 47, 6-(dipropylamino)-6,7-dihydro-2-[[4-(trifluoromethyl)phenyl]methyl]cyclopent[f]isoindole-1,3(2H,5H)-dione (108, 0.44 g, 1 mmol) was reduced with Zinc dust (1.2 g, 18.4 mmol) in glacial HOAc (20 mL). Purification using silica gel, eluting with 9:1 $CH_2Cl_2$/MeOH, afforded an oil that was converted to an HCl salt and recrystallized from methylene chloride/acetone to give 132 as a white solid (m.p. 190–192° C.).

EXAMPLE 85

6-(Dipropylamino)-2-[(4-fluorophenyl)methyl]-3,5,6,7-tetrahydrocyclopent[f]isoindol-1(2H)-one 132

Using procedure 47, 6-(dipropylamino)-2-[(4-fluorophenyl)methyl]-6,7-dihydrocyclopent[f]isoindole-1,3(2H,5H)-dione (101, 0.56 g, 1.43 mmol) was reduced with Zinc dust (0.94 g, 14.3 mmol) in glacial HOAc (20 mL). Purification using silica gel, eluting with 9:1 $CH_2Cl_2$/MeOH, afforded an oil that was converted to an HCl salt and recrystallized from EtOAc/MeOH to give 132 as a white solid (m.p. 227–228° C.).

EXAMPLE 86

Procedure 50. 4-[[6-(Dipropylamino)-3,5,6,7-tetrahydro-1-oxocyclopent[f]isoindol-2 (1H)-yl]methyl]benzonitrile 133

To a slurry of washed NaH (0.05 g, 1.32 mmol) in DMF (5 mL) was added a slurry of 6-(Dipropylamino)-3,5,6,7-tetrahydrocyclopent[f]isoindol-1(2H)-one (94, 0.30 g, 1.10 mmol) in DMF (10 mL). The slurry was heated to 84° C. and after 40 min, was treated with a solution of alpha-bromo-p-tolunitrile (0.43 g, 2.20 mmol) in DMF (10 mL). After 24 h, the reaction was quenched with $H_2O$ and extracted with $CH_2Cl_2$. The organic layers were washed with brine, dried (MgSO4), and concentrated on hi-vac. The reside was purified on silica gel, eluting with $CH_2Cl_2$/MeOH to give an oil that was converted to an HCl salt and recrystallized to afford 133 as a white solid (m.p. 141–145° C.).

EXAMPLE 87

Procedure 51: 7-(Dipropylamino)-2,3,7,8-tetrahydro-1H-cyclopenta[g]phthalazine-1,4(6H)-dione 134

A mixture of 2-(dipropylamino)-2,3-dihydro-1H-indene-5,6-dicarboxylate (92, 0.17 g, 0.5 mmol) and hydrazine hydrochloride (0.05 g, 0.7 mmol) in glacial HOAc (10 mL) was refluxed at 125° C. for 4 h. The reaction was cooled, concentrated, and converted to an HCl salt. The resulting solid was recrystallized from EtOAc/MeOH to give a white solid. This white solid was further purified via reverse phase chromatography eluting with $H_2O$/MeOH (95:5). The resulting product was converted to an HCl salt and recrystallized from hot MeOH to give 134 as a white solid (m.p.>300° C.).

EXAMPLE 88

7-(Dipropylamino)-2,3,7,8-tetrahydro-2-(phenylmethyl)-1H-cyclopenta[g]phthalazine-1,4(6H)-dione 135

Using procedure 51, 2-(dipropylamino)-2,3-dihydro-1H-indene-5,6-dicarboxylate (92, 0.349 g, 1 mmol) was treated with benzylhydrazine dihydrochloride (0.27 g, 1.4 mmol) in HOAc (20 mL) Purification using silica gel, eluting with 19:1 $CH_2Cl_2$/MeOH, afforded a solid that was converted to an HCl salt and recrystallized from EtOAc/MeOH to give 135 as a white solid (m.p. 219–220° C.).

Following are Schemes 1–3, as described above. In Scheme 1 the compounds of the invention are structurally represented as follows:

| R | Compound # |
|---|---|
| $CH_3$ | 10 |
| 4-CN-Ph | 11 |
| 4-Cl-Ph | 12 |
| 3-$NO_2$Ph | 13 |
| 3-CN-Ph | 14 |
| 4-(1-methyl-1H-imidazole) | 15 |

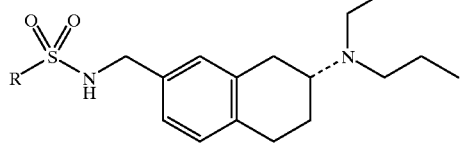

In Scheme 2 the compounds of the invention are structurally represented as follows:

| R' | Compound # |
|---|---|
| 4-Cl-Ph | 17 |
| 4-CN-Ph | 18 |

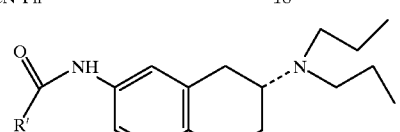

and

| R' | Compound # |
|---|---|
| 4-Cl-Ph | 20 |
| 4-CN-Ph | 21 |

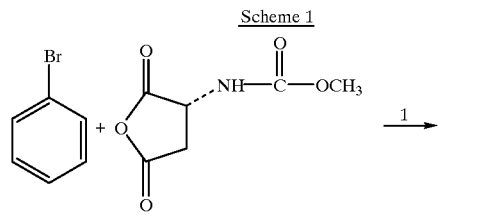

Scheme 1

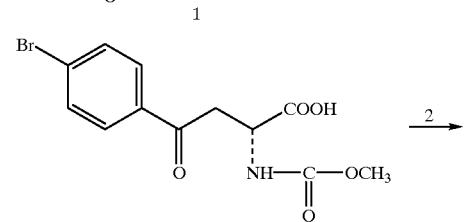

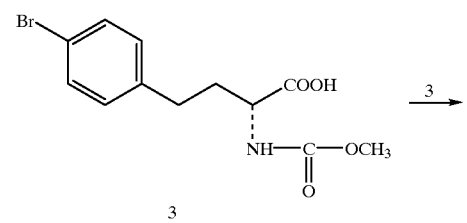

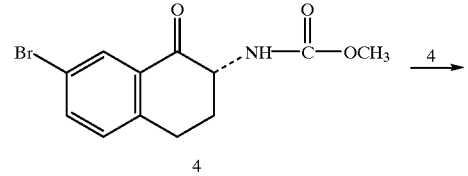

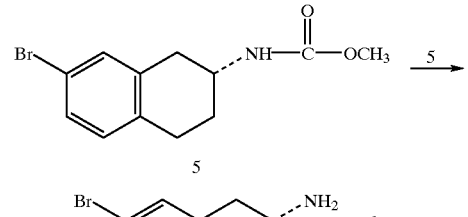

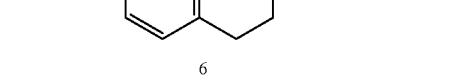

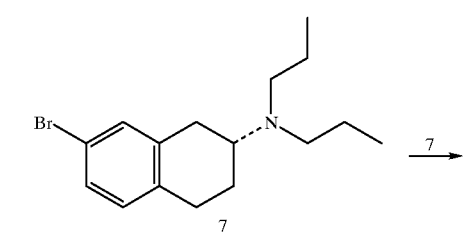
7
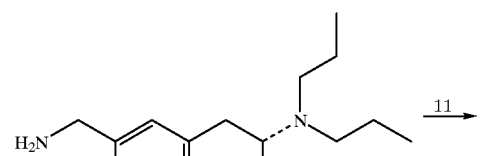
9
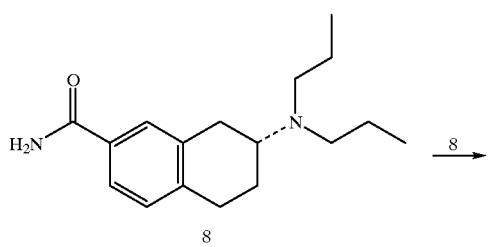
8
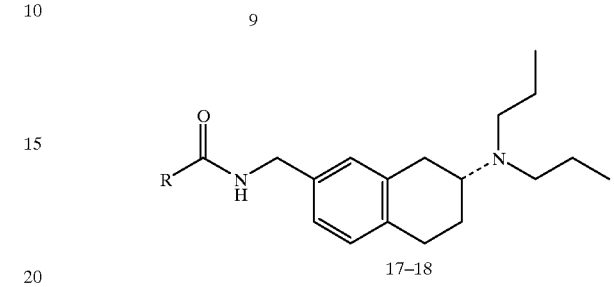
17–18
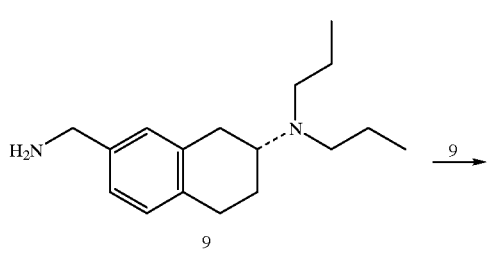
9
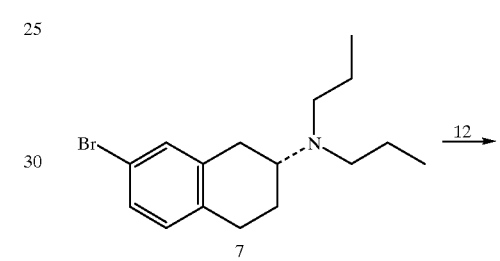
7
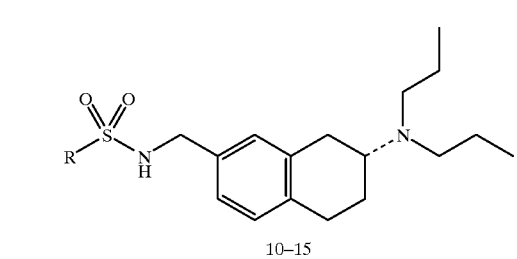
10–15
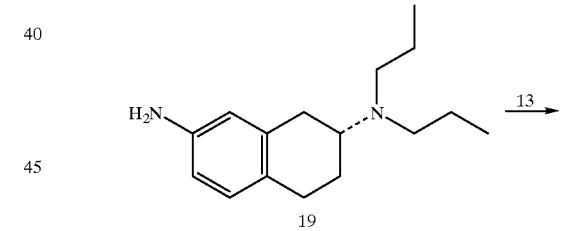
19
Scheme 2
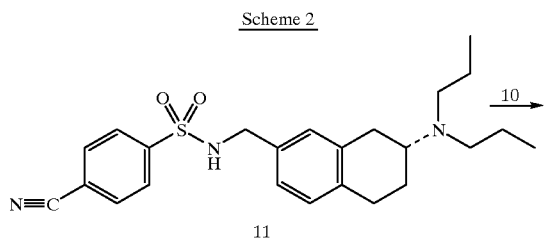
11
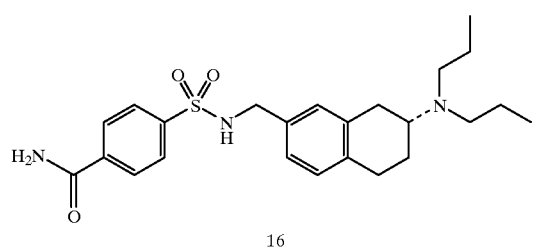
16
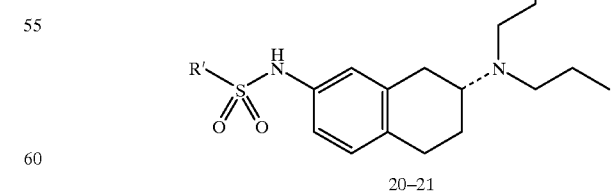
20–21

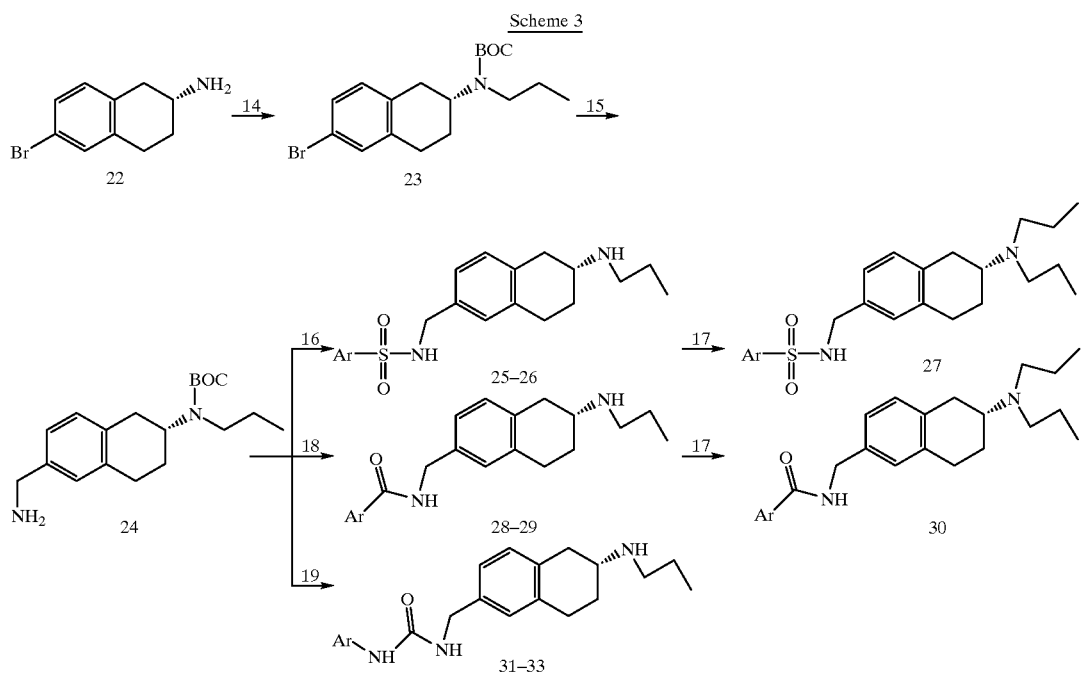
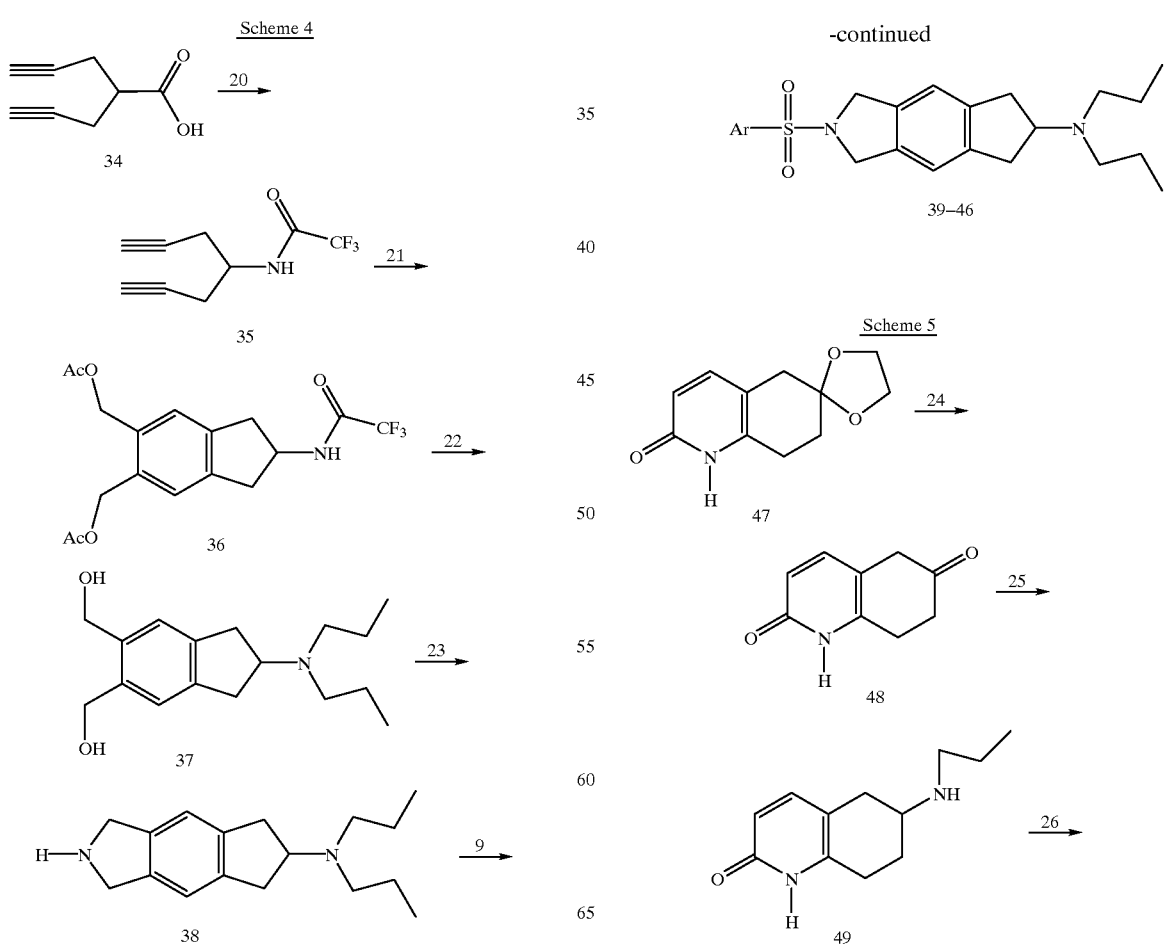

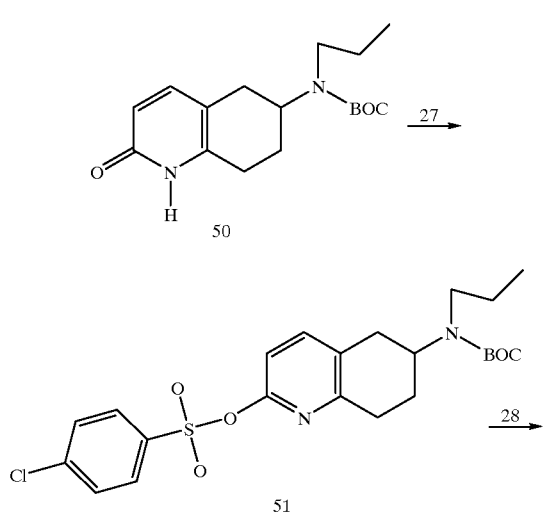
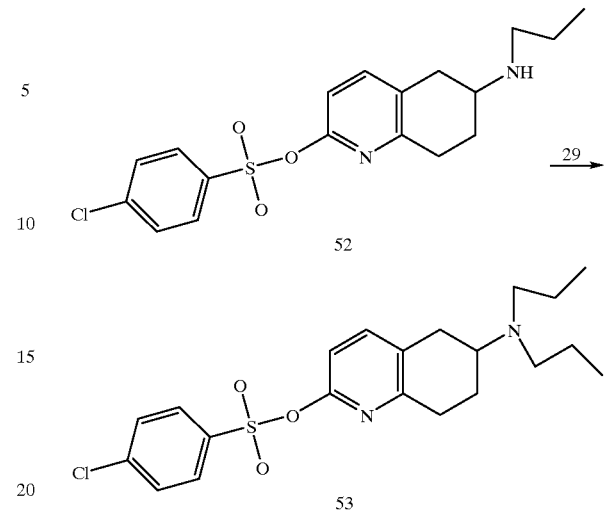
Scheme 6
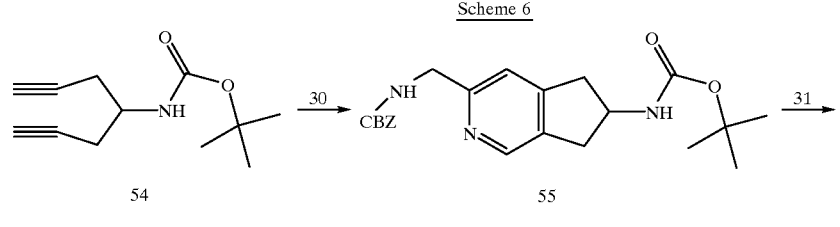
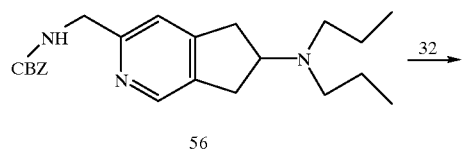
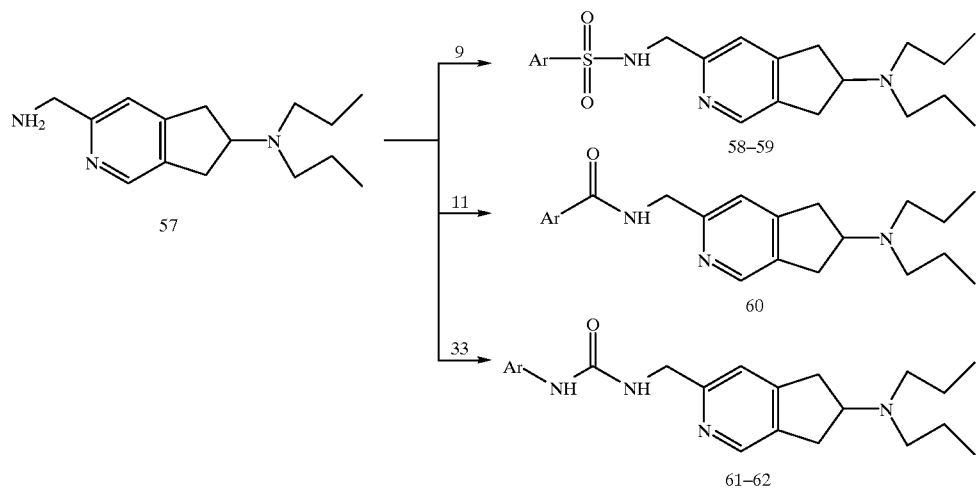

Scheme 7
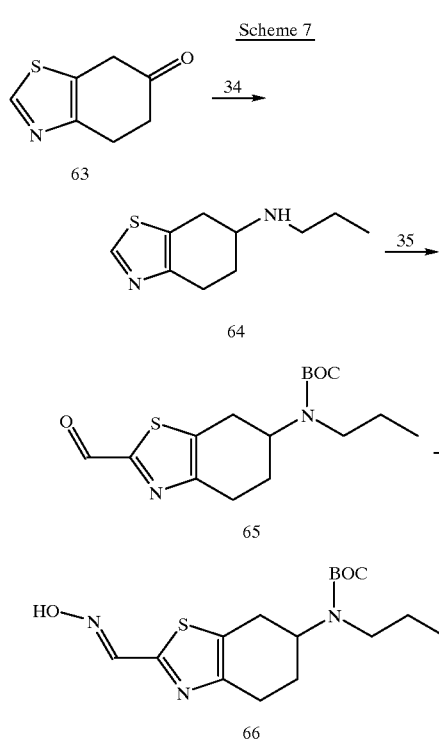
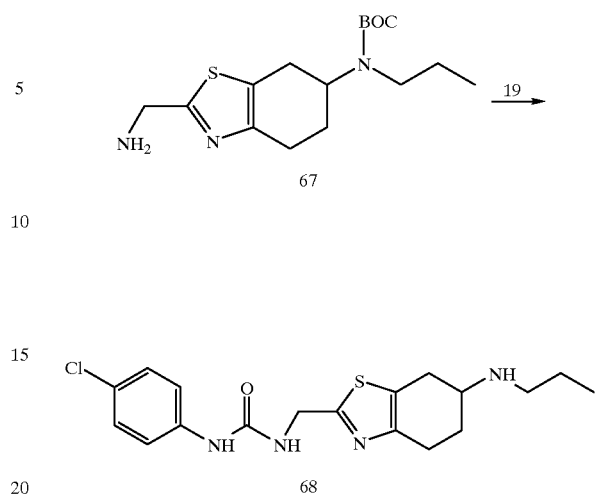
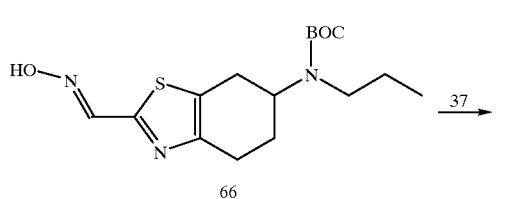
Scheme 8
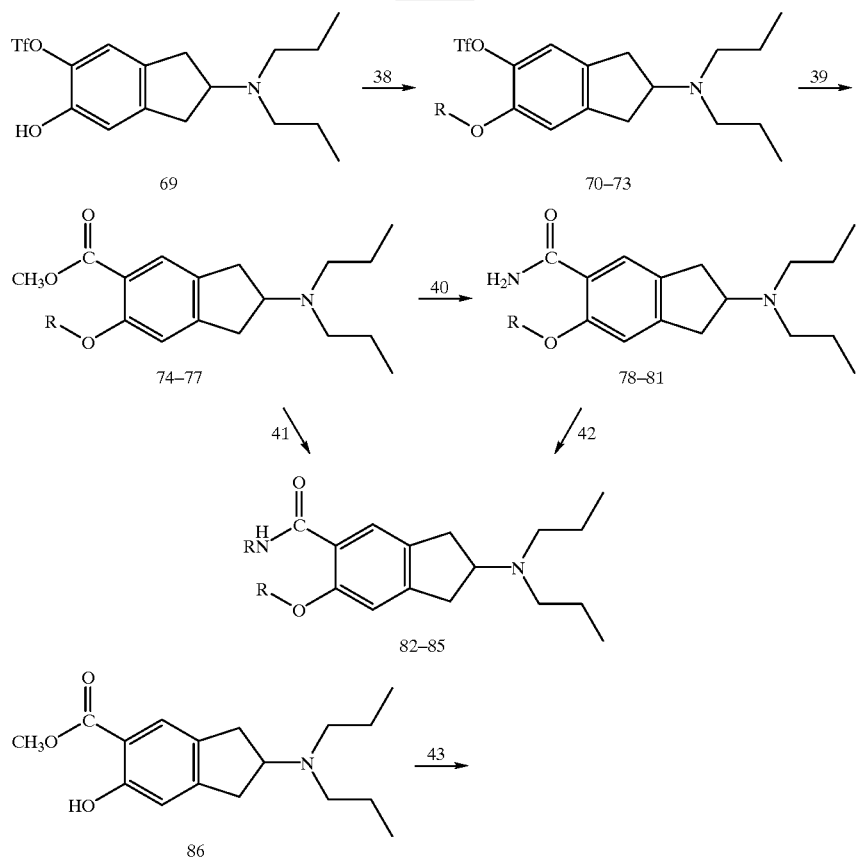

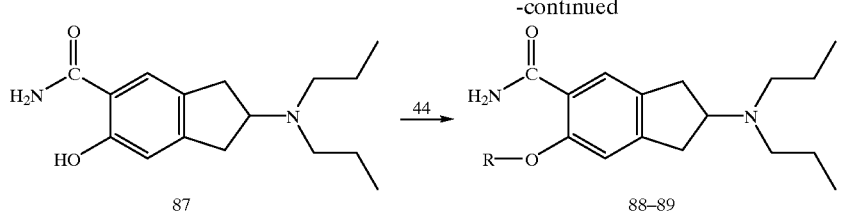

Scheme 9

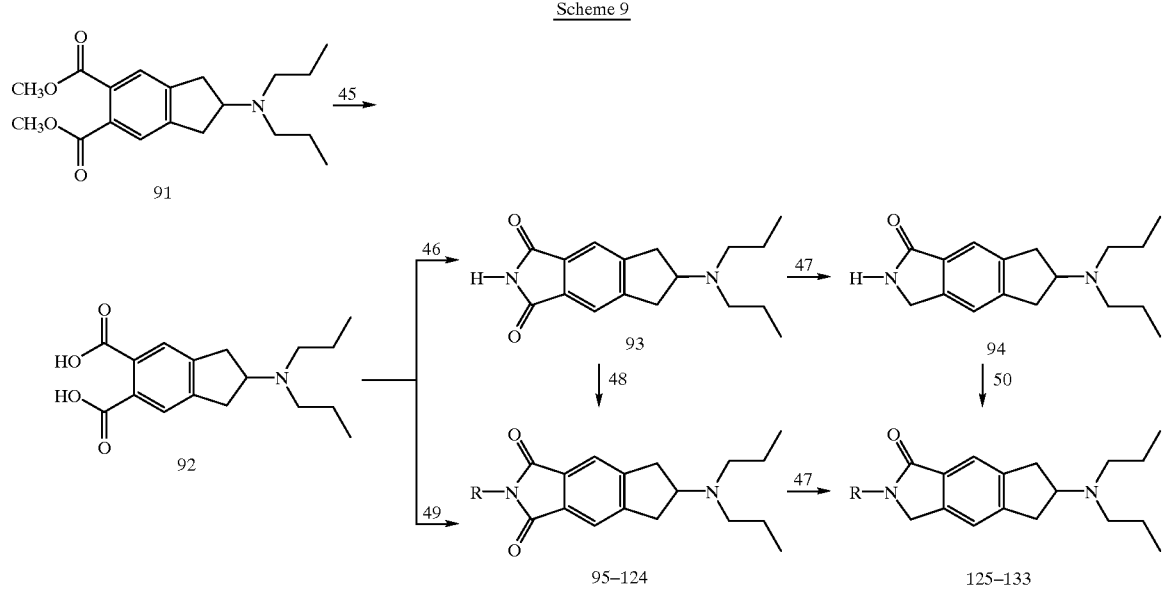

Scheme 10

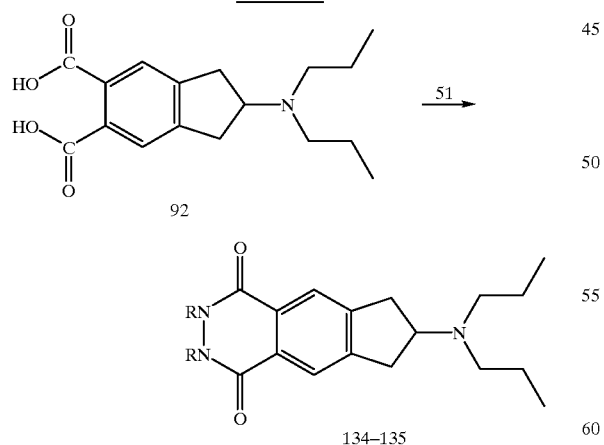

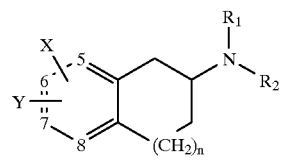

where X and Y are at the 5, 6, or 7 position wherein i) n is 1 then X is $(CH_2)_m CONR_4 R_5$, $(CH_2)_m SO_2 R_3$, $(CH_2)_m SO_2 NR_4 R_5$, $(CH_2)_m NR_4 CONHR_5$, $(CH_2)_m NHSO_2 R3$, $(CH_2)_m NHCOR_3$, or $C(O)R_4$ (where m is 0 or 1, except that where m is 0, then Y is not hydrogen or halogen); and Y is $R_4$, $(CH_2)_p CONR_4 R_5$, $(CH_2)_p CN$, $(CH_2)_p SO_2 NR_4 R_5$, $OR_6$, $(CH_2)_p SO_2 R_3$, $(CH_2)_p NHSO_2 R_3$, halogen or $(CH_2)_p NHCOR_3$ (where p is 0 or 1);

iii) n is 0 and Y is $OR_9$ then X is $(CH_2)_m CONR_4 R_5$, $(CH_2)_m SO_2 NR_4 R_5$, $(CH_2)_m NR_4 CONHR_5$, $(CH_2)_m SO_2 R_3$, $(CH_2)_m NHSO_2 R_3$ or $(CH_2)_m NHCOR_3$, $C(O)R_4$ (where m is 0 or 1); $R_1$ and $R_2$ are independently H, $C_1$–$C_8$ alkyl or $C_1$–$C_8$ alkylAryl; $R_3$ is $C_1$–$C_8$ alkyl, $C_1$–$C_6$ alkylAryl or Aryl; $R_4$ and $R_5$ are independently H, $C_1$–$C_8$ alkyl, $C_1$–$C_6$ alkylAryl or Aryl; $R_6$ is H, $C_1$–$C_8$alkyl, $C_1$–$C_6$alkylAryl, $ArylSO_2 CF_3$, $SO_2$-$C_1$–$C_8$ alkyl, $SO_2$-$C_1$–$C_6$alkylAryl, $SO_2$-Aryl;

What is claimed:

1. A compound of structural Formula I or its pharmaceutically acceptable salts:

$R_7$ is hydrogen, $CON(R_4)_2$, $SO_2N(R_4)_2$ or $SO_2R_4$;

$R_8$ is $C_1$–$C_8$ alkyl, $C_1$–$C_6$ alkylAryl, Aryl, $CON(R_4)_2$, $COR_4$, $SO_2N(R_4)_2$ or $SO_2R_4$ (provided in each case $R_4$ is not hydrogen);

$R_9$ is $C_2$–$C_8$ alkyl (optionally substituted with 1 to 3 halogens), $C_1$–$C_6$ alkylAryl, or Aryl; and $R_{10}$ is H, $C_1$–$C_8$ alkyl, $C_1$–$C_6$ alkylAryl, Aryl or $(CH_2)_{0-6}SO_2Aryl$.

2. The compound of claim 1 wherein n is 1.

3. The compound of claim 1 wherein $R_1$ and $R_2$ are independently H or $C_{1-6}$ alkyl.

4. The compound of claim 3 wherein $R_1$ and $R_2$ are both propyl.

5. The compound of claim 1 wherein Y is hydrogen.

6. The compound of claim 1 wherein X is $(CH_2)_m NHSO_2R_3$.

7. The compound of claim 6 wherein $R_3$ is phenyl optionally substituted with CN, Cl, $NO_2$ or methyl.

8. The compound of claim 1 where n is 0 and Y is $OR_9$ where $R_9$ is $C_2$–$C_8$ alkyl (optionally substituted with 1 to 3 halogens); and X is $(CH_2)_m CONR_4R_5$ where $R_4$ and $R_5$ are independently H, methyl or ethyl.

9. The compound of claim 8 which is 2-(Dipropylamino)-6-ethoxy-2,3-dihydro-1H-indene-5-carboxamide.

10. A method for treating central nervous system disorders associated with dopamine D3 receptor activity comprising:

administering to a patient in need thereof a therapeutically effective amount of a compound of Formula I of claim 1.

* * * * *